United States Patent [19]
Martin

[11] Patent Number: 5,993,403
[45] Date of Patent: Nov. 30, 1999

[54] ADJUSTABLE CERVICAL COLLAR

[75] Inventor: William Martin, Shepherdsville, Ky.

[73] Assignee: Ambu International A/S, Glostrup, Denmark

[21] Appl. No.: 09/041,594

[22] Filed: Mar. 13, 1998

Related U.S. Application Data

[63] Continuation of application No. 08/652,936, May 24, 1996, Pat. No. 5,728,054, which is a continuation of application No. 08/199,366, Feb. 18, 1994, Pat. No. 5,520,619, which is a continuation-in-part of application No. 08/064,221, May 20, 1993, Pat. No. 5,366,438.

[51] Int. Cl.⁶ ...................................................... A61F 5/00
[52] U.S. Cl. ...................................... 602/18; 128/DIG. 23
[58] Field of Search ................ 602/18, 19; 128/DIG. 23

[56] References Cited

U.S. PATENT DOCUMENTS

| | | |
|---|---|---|
| 2,102,069 | 12/1937 | Hanicke . |
| 2,692,595 | 10/1954 | Blair, Jr. . |
| 2,735,424 | 2/1956 | Benjamin . |
| 2,736,314 | 2/1956 | Hale . |
| 2,801,630 | 8/1957 | Moore . |
| 2,806,471 | 9/1957 | Breese . |
| 2,807,260 | 9/1957 | Teufel . |
| 2,818,063 | 12/1957 | Smith et al. . |
| 2,820,455 | 1/1958 | Hall ........................................... 602/18 |
| 2,828,736 | 4/1958 | Monfardini . |
| 2,904,040 | 9/1959 | Hale . |
| 2,911,970 | 11/1959 | Bartels . |
| 3,024,784 | 3/1962 | Monfardini . |

(List continued on next page.)

FOREIGN PATENT DOCUMENTS

| | | |
|---|---|---|
| 1132607 | 11/1968 | Australia . |
| 8112343 | 6/1981 | France . |
| 8123436 | 12/1981 | France . |
| 2 507 887 | 12/1982 | France . |
| 918770 | 2/1955 | Germany . |
| 1199921 | 9/1965 | Germany . |
| 2129140 | 12/1972 | Germany . |
| 2404683 C3 | 8/1975 | Germany . |
| 3308571 A1 | 9/1984 | Germany . |
| 3318938 A1 | 11/1984 | Germany . |
| 3929347 A1 | 3/1990 | Germany . |
| 3905115 A1 | 8/1990 | Germany . |
| 3906233 A1 | 8/1990 | Germany . |
| 2 049 436 | 12/1980 | United Kingdom . |
| 2 165 157 | 4/1986 | United Kingdom . |
| 2 165 762 | 4/1986 | United Kingdom . |
| 2 182 851 | 5/1987 | United Kingdom . |
| 2 233 900 | 1/1991 | United Kingdom . |
| 2 234 905 | 2/1991 | United Kingdom . |

*Primary Examiner*—Michael A. Brown
*Attorney, Agent, or Firm*—Levy & Grandinetti

[57] ABSTRACT

An improved cervical collar comprised of an elongated neck encircling band, a chin support brace, a sternum and shoulder brace and an adjustment system secured to the sternum and shoulder brace and the elongated neck encircling band for adjusting the height of the sternum and shoulder brace in relation to the elongated neck encircling band. The adjustment system is designed to lock the sternum and shoulder brace in position preventing further extension of the sternum and shoulder brace in relation to the elongated neck encircling band as well as preventing retrograde movement of the sternum and shoulder brace in relation to the neck encircling band. The collar also comprises a positive alignment tracking system for maintaining the sternum and shoulder brace in parallel alignment with the elongated neck encircling band as the height of the sternum and shoulder brace is adjusted. In an alternative embodiment the sternum and shoulder brace is an integral part of the elongated neck encircling band and the chin support brace is secured to a chin support height adjustment piece which is slidably secured to the elongated neck encircling band such that the height of the elongated neck encircling band and the sternum and shoulder brace are adjustable together and independent from the chin support height adjustment piece.

20 Claims, 13 Drawing Sheets

U.S. PATENT DOCUMENTS

| | | |
|---|---|---|
| 3,027,894 | 4/1962 | Moore . |
| 3,042,026 | 7/1962 | Monfardini . |
| 3,042,027 | 7/1962 | Monfardini . |
| 3,050,052 | 8/1962 | Grassl . |
| 3,055,358 | 9/1962 | Di Palma et al. . |
| 3,070,090 | 12/1962 | Taylor . |
| 3,135,256 | 6/1964 | Gruber . |
| 3,164,151 | 1/1965 | Nicoll . |
| 3,220,406 | 11/1965 | Connelly ................................. 602/18 |
| 3,285,243 | 11/1966 | Yellin . |
| 3,285,244 | 11/1966 | Cottrell . |
| 3,295,516 | 1/1967 | Grassl . |
| 3,306,284 | 2/1967 | McKinley . |
| 3,313,297 | 4/1967 | Applegate et al. . |
| 3,320,950 | 5/1967 | McElvenny . |
| 3,343,532 | 9/1967 | Zumaglini . |
| 3,364,926 | 1/1968 | Alderson . |
| 3,374,785 | 3/1968 | Gaylord, Jr. . |
| 3,397,688 | 8/1968 | Gottfried . |
| 3,504,667 | 4/1970 | McFarlane . |
| 3,507,273 | 4/1970 | Yellin . |
| 3,512,523 | 5/1970 | Barnett . |
| 3,530,853 | 9/1970 | Bond . |
| 3,572,328 | 3/1971 | Bond . |
| 3,696,810 | 10/1972 | Gaylord, Jr. . |
| 3,724,452 | 4/1973 | Nitschke ................................. 602/18 |
| 3,756,226 | 9/1973 | Calabrese et al. . |
| 3,850,164 | 11/1974 | Hare . |
| 3,905,362 | 9/1975 | Eyrick et al. . |
| 3,916,884 | 11/1975 | Attenburrow . |
| 3,916,885 | 11/1975 | Gaylord, Jr. . |
| 3,921,626 | 11/1975 | Neel . |
| 3,964,474 | 6/1976 | Fox . |
| 4,041,940 | 8/1977 | Frankel et al. . |
| 4,043,325 | 8/1977 | Ochs et al. . |
| 4,141,368 | 2/1979 | Meyer . |
| 4,194,501 | 3/1980 | Watt . |
| 4,204,529 | 5/1980 | Cochrane . |
| 4,232,663 | 11/1980 | Newton . |
| 4,299,209 | 11/1981 | Behrens et al. . |
| 4,325,363 | 4/1982 | Berkeley . |
| 4,383,523 | 5/1983 | Schurman . |
| 4,401,111 | 8/1983 | Blackstone . |
| 4,515,153 | 5/1985 | Calabrese . |
| 4,520,801 | 6/1985 | Lerman . |
| 4,538,597 | 9/1985 | Lerman . |
| 4,543,947 | 10/1985 | Blackstone . |
| 4,562,833 | 1/1986 | Pujals, Jr. . |
| 4,582,051 | 4/1986 | Greene et al. . |
| 4,589,407 | 5/1986 | Koledin et al. . |
| 4,628,913 | 12/1986 | Lerman . |
| 4,643,174 | 2/1987 | Horiuchi . |
| 4,643,719 | 2/1987 | Garth et al. . |
| 4,702,233 | 10/1987 | Omicioli . |
| 4,708,129 | 11/1987 | Pujals, Jr. . |
| 4,782,824 | 11/1988 | Davies ...................................... 602/18 |
| 4,794,917 | 1/1989 | O'Leary . |
| 4,819,622 | 4/1989 | Taylor et al. . |
| 4,827,915 | 5/1989 | Gorsen . |
| 4,886,052 | 12/1989 | Calabrese . |
| 4,940,043 | 7/1990 | Burns et al. . |
| 4,955,368 | 9/1990 | Heimann . |
| 4,969,453 | 11/1990 | Heimann . |
| 4,987,891 | 1/1991 | Gaylord, Jr. et al. . |
| 5,003,968 | 4/1991 | Mars . |
| 5,005,563 | 4/1991 | Veale . |
| 5,005,564 | 4/1991 | Grundei et al. . |
| 5,010,877 | 4/1991 | Druskoczi . |
| 5,029,577 | 7/1991 | Sarkozi . |
| 5,038,759 | 8/1991 | Morgenstern . |
| 5,048,509 | 9/1991 | Grundei et al. . |
| 5,054,475 | 10/1991 | Calabrese et al. . |
| 5,058,572 | 10/1991 | Schmid et al. . |
| 5,060,637 | 10/1991 | Schmid et al. . |
| 5,083,553 | 1/1992 | Stevenson . |
| 5,163,941 | 11/1992 | Garth et al. . |
| 5,171,296 | 12/1992 | Herman . |
| 5,211,185 | 5/1993 | Garth et al. . |
| 5,215,517 | 6/1993 | Stevenson et al. . |

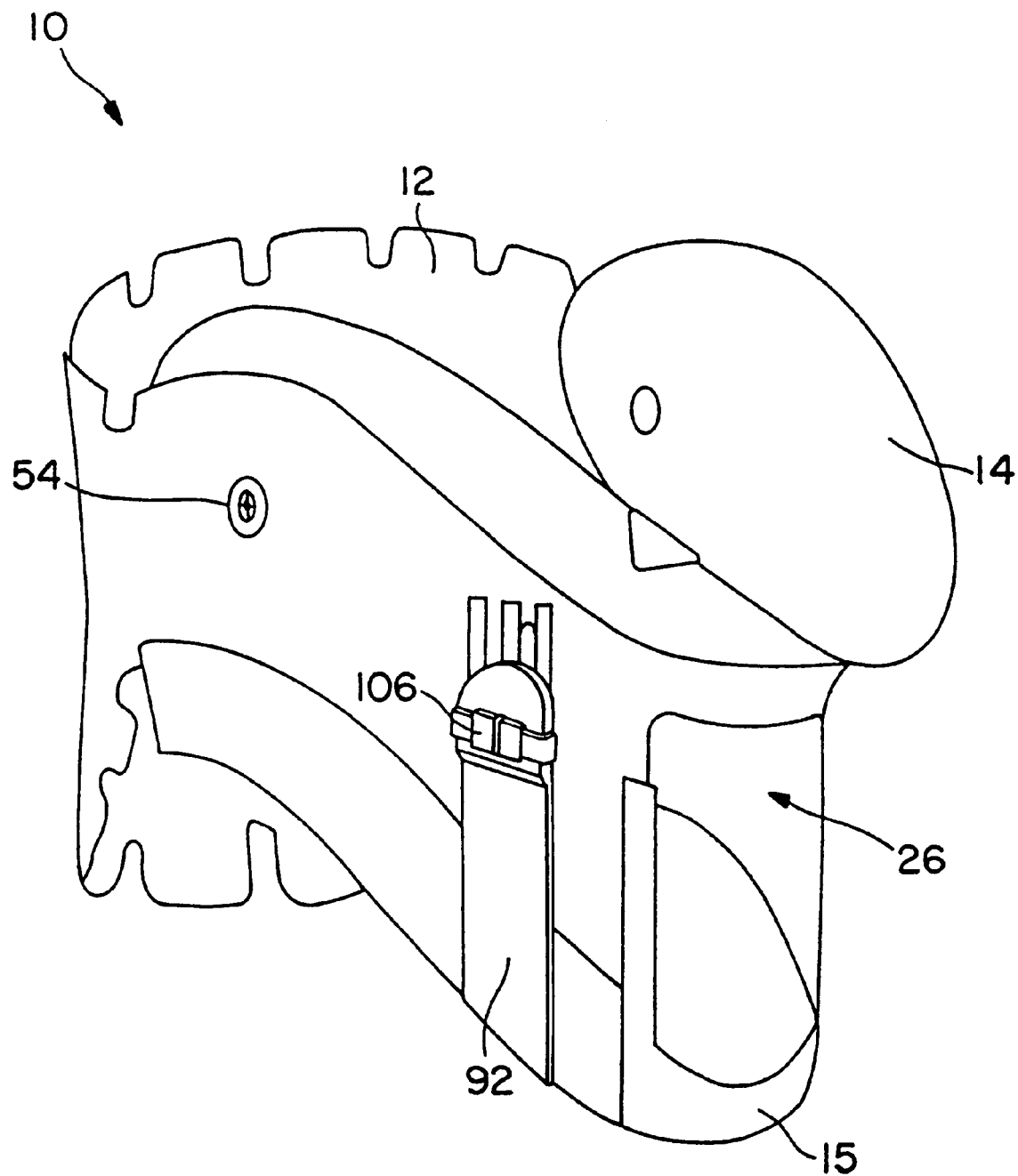
FIG. IC

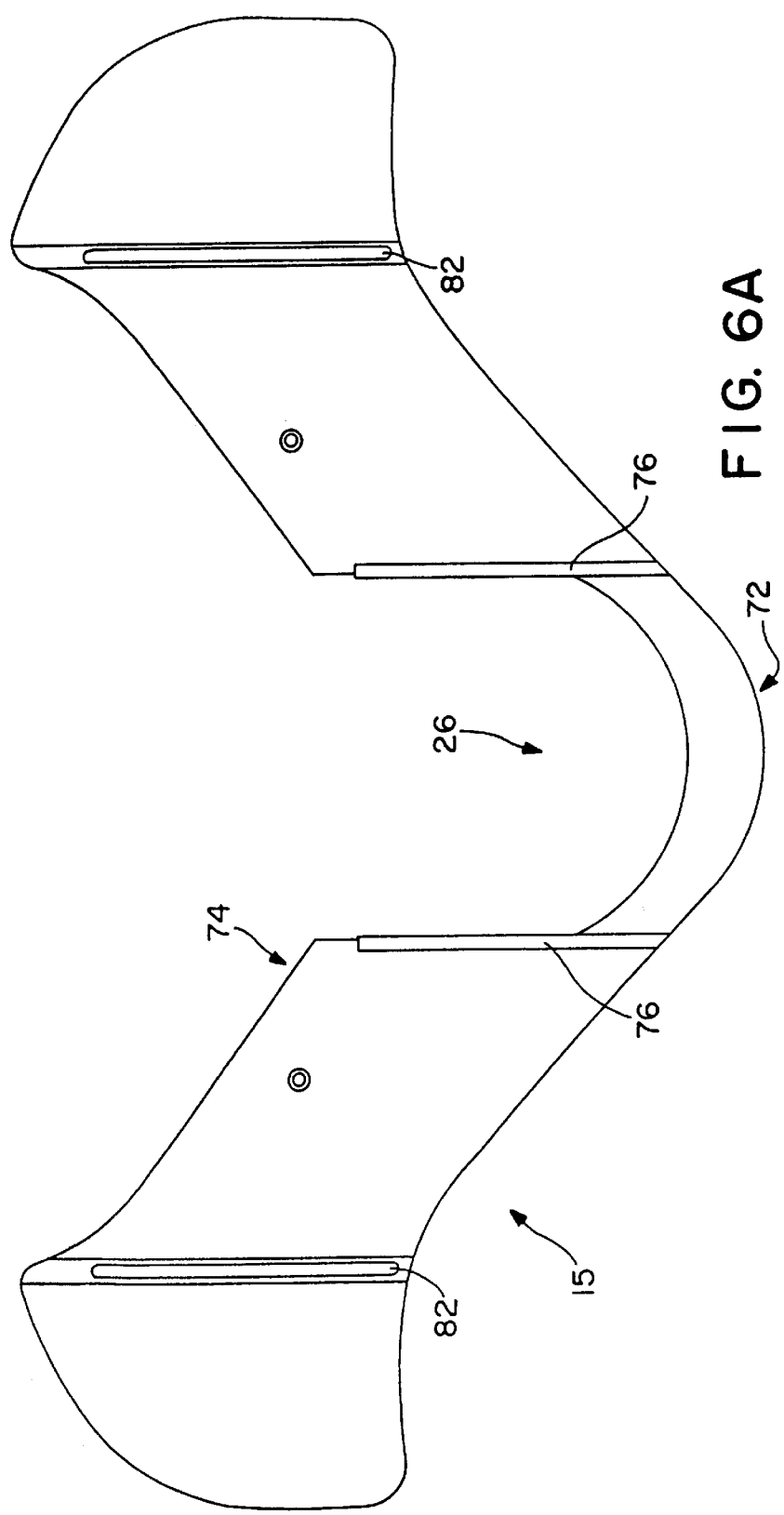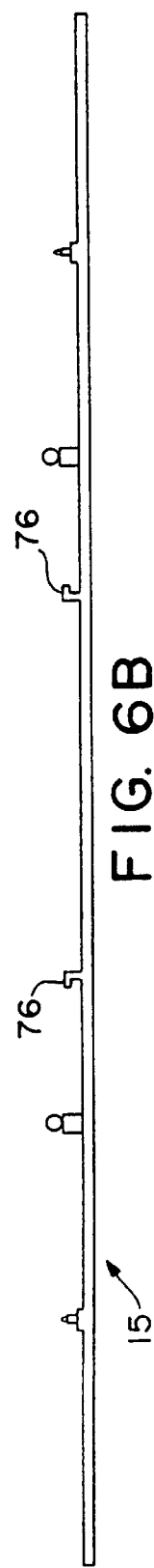

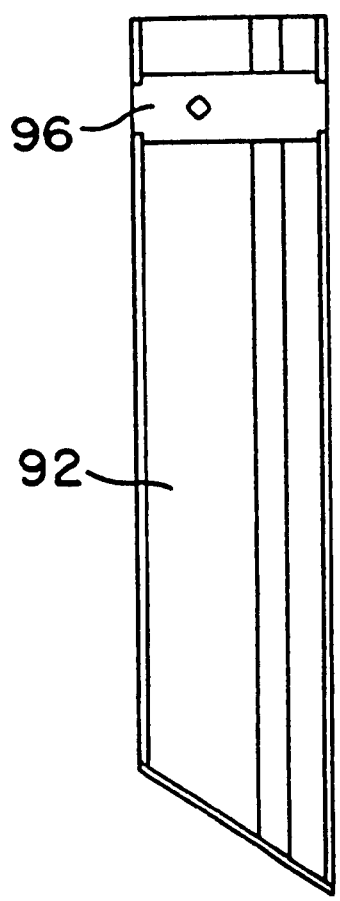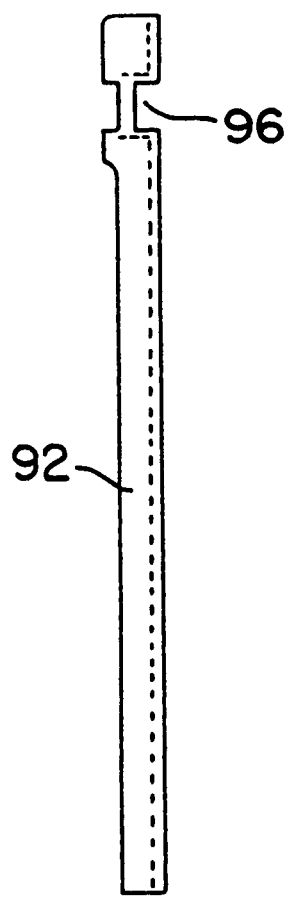
FIG. 8A      FIG. 8B
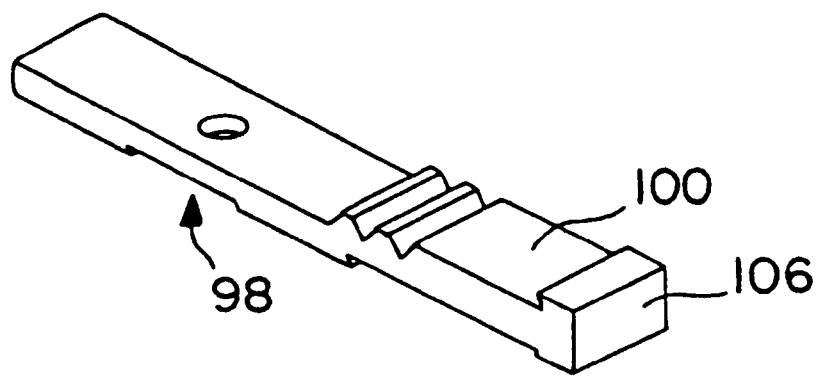
FIG. 9

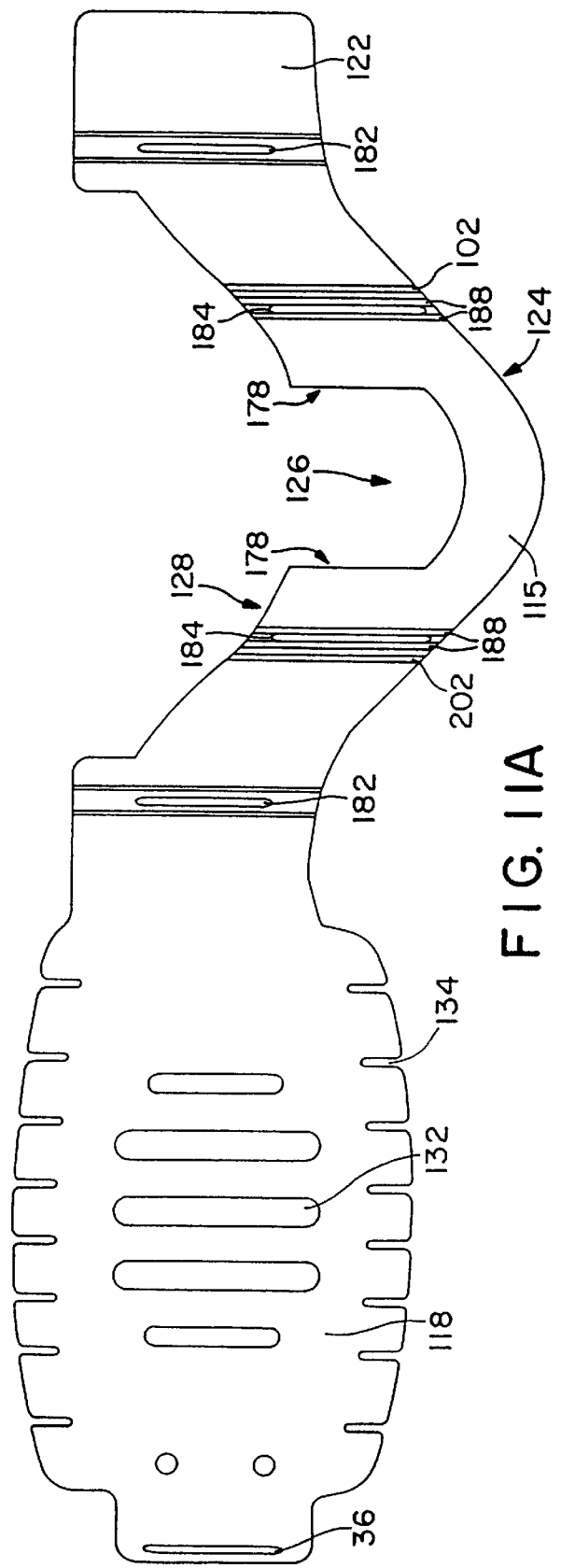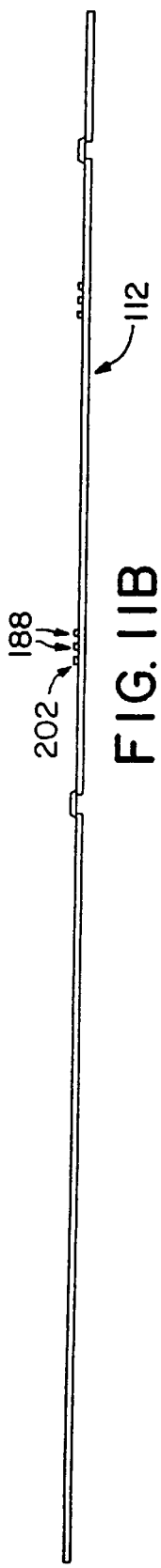
FIG. 11A
FIG. 11B

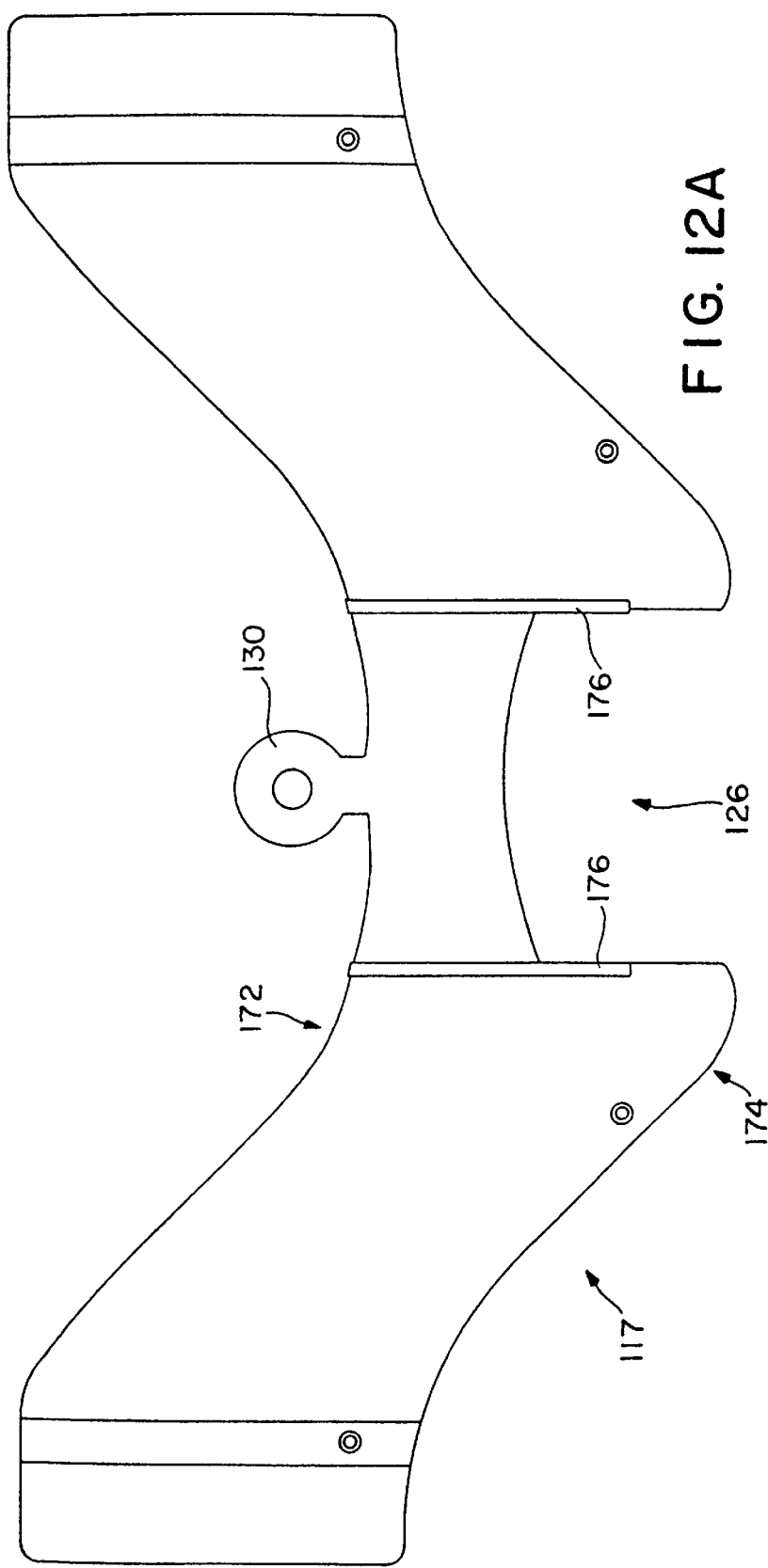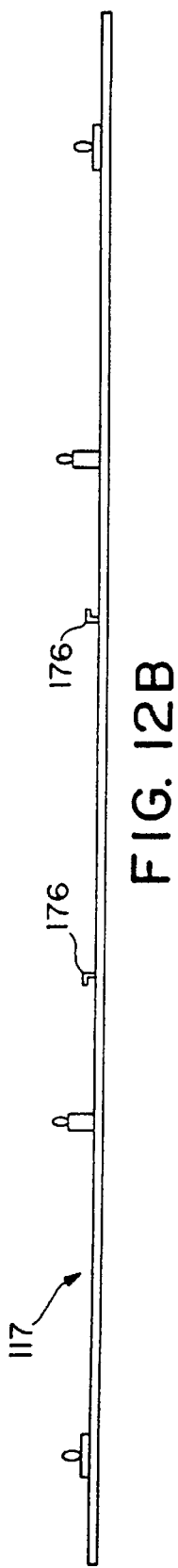
FIG. 12A
FIG. 12B

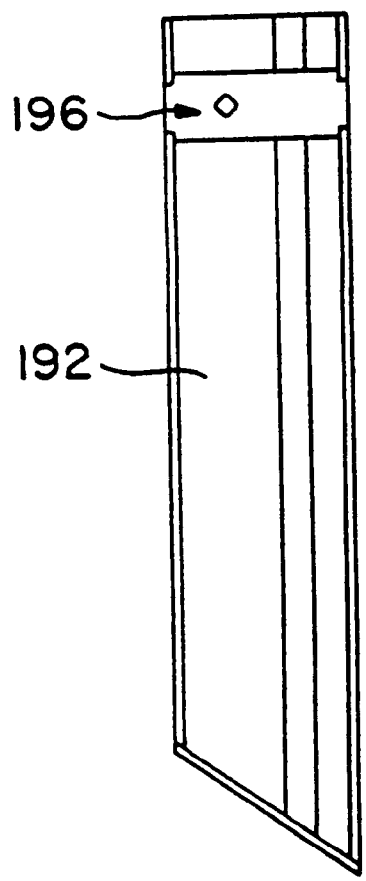 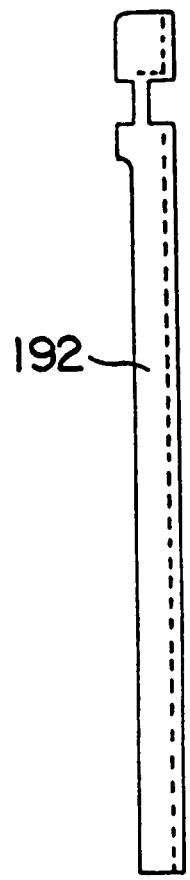
FIG. 17A    FIG. 17B
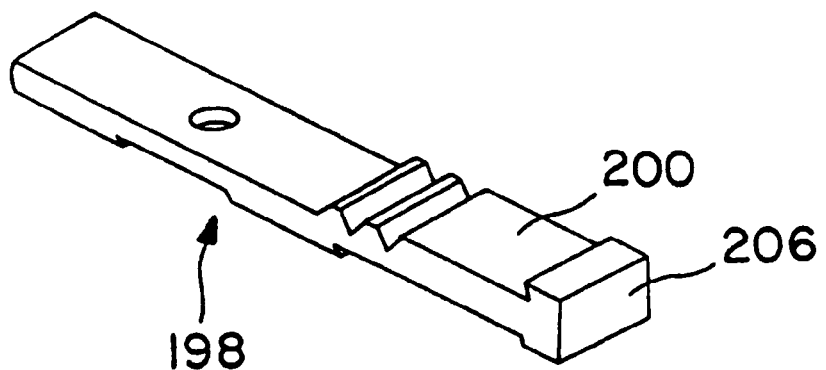
FIG. 18

ADJUSTABLE CERVICAL COLLAR

This application is a continuation application of U.S. application Ser. No. 08/652,936 filed on May 24, 1996, now U.S. Pat. No. 5,728,054, which was a continuation application of U.S. application Ser. No. 08/199,366, filed on Feb. 18, 1994, now U.S. Pat. No. 5,520,619, which was a continuation-in-part application of U.S. application Ser. No. 08/064,221, filed on May 20, 1993, now U.S. Pat. No. 5,366,438.

BACKGROUND OF INVENTION

1. Field of Invention

This invention relates to cervical collars. More specifically this invention relates to a cervical collar with an adjustable sternum and shoulder brace.

2. Prior Art

Numerous types of cervical collars have been disclosed which are designed to restrict the movement of the head and neck of a person who has suffered a neck or spinal injury. In fact, cervical collars are now standard equipment for emergency medical service squads and rescue units.

Originally cervical collars were constructed from relatively heavy strap-like materials such as leather or other such heavy duty materials and usually included a number of metal braces. See, for example, U.S. Pat. No. 3,027,894. These bulky cervical collars were reasonably successful in immobilizing the head but presented significant problems when x-rays were needed because of the metal contained within the braces. In addition, these bulky cervical collars did not provide access to the patient's neck if a tracheotomy was necessary. Finally, because of the materials commonly used to manufacture these bulky collars, they were cumbersome to use and expensive to produce. Because of current and anticipated limitations on reuse of virtually all medical products, expense is now a significant factor in the choice of all medical equipment which may be exposed to body fluids, including specifically cervical collars. Thus, these bulky cervical collars are now too expensive as single use, medical products.

As a result of the enhanced utilization of lighter weight, plastic materials, cervical collars are now generally constructed from relatively stiff, light-weight plastic materials that are capable of being bent to encircle the neck of the wearer and yet still provide substantial support for the wearer. Examples of these types of collars are disclosed, for example, in U.S. Pat. Nos. 5,083,553, 5,060,637 and U.S. Pat. No. RE. 32,219.

In emergency medical situations, it may be necessary to install a low cost, cervical collar on individuals of varying sizes. For example, a cervical collar may be necessary for a child of small size or a large adult. As a result, it is important that the size of the cervical collar be adjustable and yet still effectively immobilize the neck of the patient. This problem has been partially addressed by providing different size cervical collars for different sized individuals.

When placing a cervical collar on an injured individual, it is also helpful to put the cervical collar in position behind the patient and then adjust the frontal portion of the cervical collar to immobilize the neck of the patient regardless of the patient's size. As a result, a number of cervical collars have been designed which permit the neck supporting piece or sternum and shoulder brace to be expanded to better support the patient's neck. Early models of these cervical devices such as U.S. Pat. Nos. 3,024,784 and 3,060,930 allow for the vertical extension of the neck supporting piece or sternum and shoulder brace of the cervical collar utilizing conventional construction. In addition, modest adjustments to the location of the neck piece of a cervical collar have been disclosed more recently in U.S. Pat. Nos. 4,520,801 and 5,180,361.

A common element of cervical collars and also cervical braces are structural designs for adjustment of the position of the neck support of a sternum and shoulder brace or cervical collar. In cervical braces a brace element is placed around the shoulders of the patient, a neck piece is placed under the patient's neck and the distance between those two is adjusted by adjustment means such as screw and bolt, pins and other such adjustment devices. See, for example, U.S. Pat. Nos. 2,102,069, 2,736,314, 3,024,784, 3,306,284, 3,724,452, 4,515,153, 4,628,913 and British Patent Nos. 1,132,607 and 2,233,900. Other common methods for adjusting the height and placement of the neck piece of a cervical collar have also been disclosed, for example in U.S. Pat. Nos. 2,828,736, 3,027,894, 3,042,027, 3,295,516, 3,220,406, 3,313,297 and 3,916,885.

While many of these patents disclose devices which have neck support pieces or sternum and shoulder braces that are adjustable, they are not easily adaptable for placement around the patient in an emergency medical situation. In addition, these devices do not provide adjustable neck support pieces which can be adjusted in height while the back portion of the cervical collar is held in place against the patient's neck. Further, these devices fail to provide adjustable neck support pieces that can be locked in position thus preventing the patient from collapsing the cervical collar after it is installed in place. Further, the disclosed devices for adjusting the neck support or sternum and shoulder brace fail to permit parallel adjustment to both sides of neck support or sternum and shoulder braces automatically.

Therefore, it is an object of this invention to provide an improved cervical collar.

It is a further object of this invention to provide a cervical collar with an improved sternum and shoulder brace for said collar.

It is a still further object of this invention to provide an improved cervical collar whose neck sternum and shoulder brace can be adjusted.

It is a still further object of this invention to provide an improved cervical collar with an adjustable sternum and shoulder brace which can be locked in a fixed position.

It is a still further object of this invention to provide an improved cervical collar with an adjustable sternum and shoulder brace which provides positive parallel adjustment to both sides of the sternum and shoulder brace automatically.

It is a still further object of this invention to provide an improved cervical collar with an adjustable sternum and shoulder brace which can be adjusted in height while the back portion of the cervical collar is held in place against the patient's neck.

It is a still further object of this invention to provide an improved cervical collar with an adjustable sternum and shoulder brace and a chin support brace wherein the chin support brace can be adjusted in height while the back portion of the cervical collar and the sternum and shoulder brace are held in place against the patient.

These and other objects and features of the present invention will become apparent to those skilled in the art from a consideration of the following detailed description, drawings and claims. The description, along with the accompanying drawings, provide selected examples of the construction of the device to illustrate the invention.

SUMMARY OF INVENTION

In accordance with the present invention there is provided an improved cervical collar comprised of an elongated neck encircling band, a chin support brace and an adjustable sternum and shoulder brace with an adjustment system means for adjusting the height of the sternum and shoulder brace in relation to the elongated neck encircling band. The adjustable sternum and shoulder brace can be adjusted in height in relation to the chin support brace and can be locked in a fixed position to support the neck of the patient. While the preferred embodiment utilizes a separate elongated neck encircling band, chin support brace and adjustable sternum and shoulder brace, the chin support brace may be formed at the same time as or formed as an integral unit of the elongated neck encircling band.

In an alternative embodiment the present invention is an improved cervical collar comprised of an elongated neck encircling band which includes as an element thereof a sternum and shoulder brace, a chin support height adjustment piece, a chin support brace secured to said chin support height adjustment piece and an adjustment system means for adjusting the height of the chin support brace in relation to the elongated neck encircling band. The height of the chin support brace can be adjusted in relation to the elongated neck encircling band and then locked in a fixed position to support the neck of the patient.

This invention will now be described with reference to the accompanying drawings in which FIG. 1A is a front plan view of the cervical collar in its flat position.

FIG. 6A is a front plan view of the sternum and shoulder brace of the cervical collar.

FIG. 6B is an end view of the sternum and shoulder brace of the cervical collar.

FIG. 8A is the front plan view of the cover piece of the cervical collar.

FIG. 8B is a side view of the cover piece of the cervical collar.

FIG. 9 is the slide piece containing a pawl for use with the cervical collar.

FIG. 11A is a front plan view of the alternative embodiment of the elongated neck encircling band in its flat position with sternum and shoulder brace.

FIG. 11B is an edge view of the alternative embodiment of the elongated neck encircling band with sternum and shoulder brace.

FIG. 12A is a front plan view of the chin support height adjustment piece of the alternative embodiment of the cervical collar in its flat position.

FIG. 12B is an edge view of the chin support height adjustment piece of the alternative embodiment of the cervical collar in its flat position.

FIG. 17A is the front plan view of the alternative embodiment of the cover piece of the cervical collar.

FIG. 17B is a side view of the alternative embodiment of the cover piece of the cervical collar.

FIG. 18 is the slide piece of the alternative embodiment containing a pawl for use with the cervical collar.

DETAILED DESCRIPTION OF THE PREFERRED EMBODIMENT

Figure 1A:
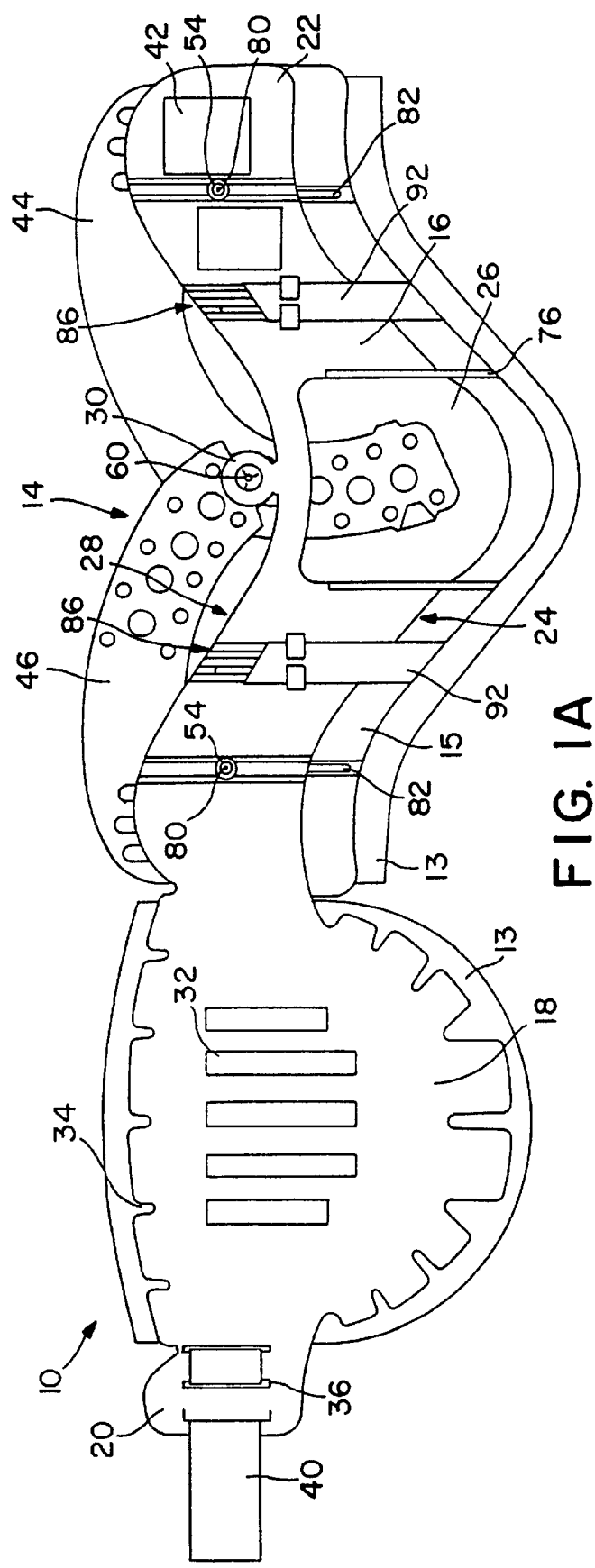
FIG. 1B is an edge view of the cervical collar in its flat position.
FIG. 1C is a side perspective view of the cervical collar with the chin support brace in its bowed forward position.

Although the invention is adaptable to a wide variety of uses, it is shown in the accompanying drawings for purpose of illustration as embodied in the improved cervical collar (10) comprised of an elongated neck encircling band (12), a chin support brace (14) and an adjustable sternum and shoulder brace (15) with adjustment system for adjusting the height of the sternum and shoulder brace in relation to the elongated neck encircling band (12). See FIG. 1A.

The elongated neck encircling band (12) is formed from a stiff, plastic sheet material such as high density polyethylene, polyvinyl chloride or other such stiff, sturdy plastic material. The elements of the cervical collar may be die cut, extruded or prepared from molds as is conventional in the industry. For comfort there may be secured to the inner surface of this stiff plastic at various locations soft, foam type pads (13) which are comprised of conventional soft plastic material. These soft plastic pads are secured to the stiff plastic material by any conventional securing means such as an adhesive or snap fasteners. It is preferred that these foam pads be secured by cement or other adhesive to reduce the number of parts of the cervical collar (10).

Figure 2:
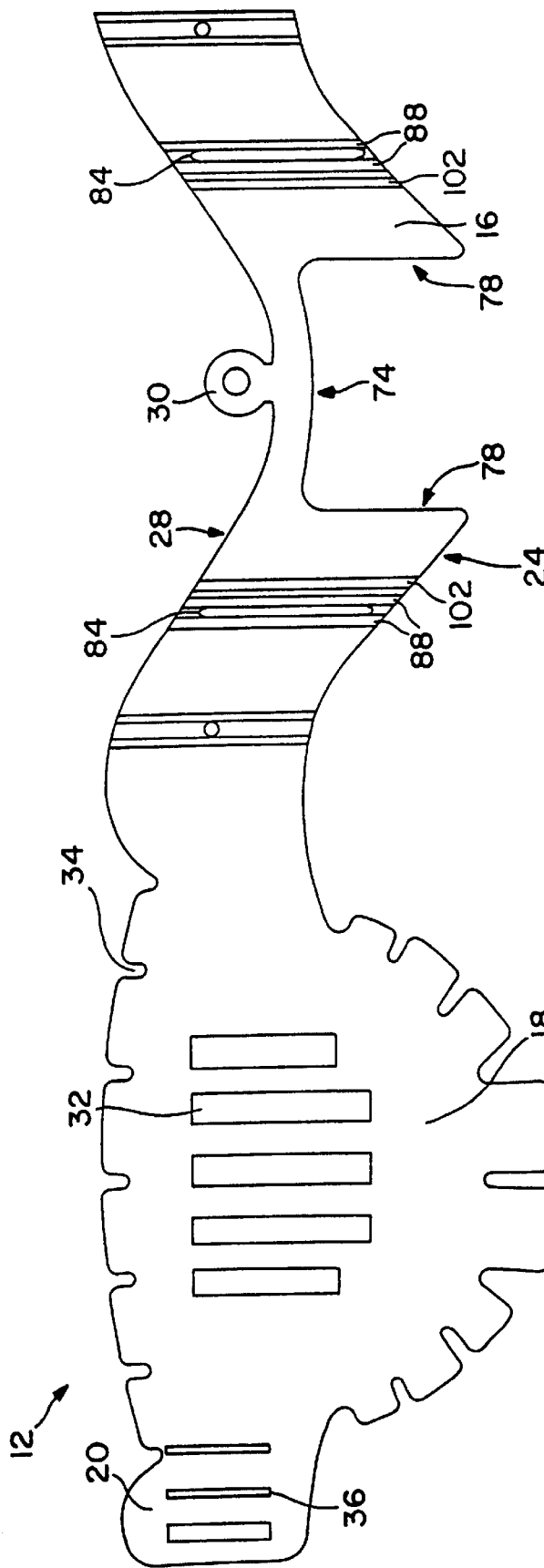
FIG. 2 is the elongated neck encircling band of the cervical collar.

The elongated neck encircling band (12) is preferably of one-piece construction generally comprised of a frontal portion (16) a back portion (18), a back side portion (20) and a front end portion (22). See FIG. 2. The elongated neck encircling band (12) is asymmetrical in design with the frontal portion (16) attached to, and an integral part of, the back portion (18).

The frontal portion (16), which has affixed to it the chin support brace (14), will be placed against the user of the cervical collar on the front portion of the user's neck under the user's chin. The back portion (18) of the cervical collar (10) is generally affixed to the back of the user's neck. The back side portion (20) and the front end portion (22) are integral elements of the neck encircling band (12) located at each end and are generally secured together after the improved cervical collar is secured to the wearer. See FIG. 2.

The frontal portion (16) when placed flat is generally curvilinear in design, curving downward and then generally curving back upward from the front end portion (22) to the back portion (18) with an opposite longitudinal curved edge which runs from one side of the frontal portion to the other side. See FIG. 2. The lower curved edge (24) of the frontal portion is discontinued at that point where a cut-out section (26), which in use overlaps the Adams' apple or larynx of the wearer is formed, to permit a tracheotomy to be performed through the cut-out section (26) with the cervical collar (10) in place. The upper curved edge (28) of the frontal portion (16) runs roughly parallel to the lower curved edge (24) except that it is not discontinued as with the lower curved edge (24).

Secured to the upper curved edge (28) is a chin support tab (30) extending upward away from the upper curved edge (28) of the frontal portion. This chin support tab (30) is used to secure the chin support brace (14) to the frontal portion (16) of the neck encircling band (12). See FIGS. 1A and 2.

Secured to one side of the frontal portion and an integral part of the cervical collar is the back portion (18) of the cervical collar (10). The back portion (18) can be of any conventional shape from generally rectangular to generally oval. The back portion (18) of the elongated neck encircling band (12) contains a number of vertical elongated slots (32) and cooperating slits (34) to make the neck encircling band (12) more flexible. These slots (32) are generally cut-out sections contained in the body of the back portion (18) running horizontally from near where the frontal portion (16) joins the back portion (18) to the opposite side of the back portion. These slots (32) are generally located in the body of the back portion (18) running approximately half way the distance between the top and the bottom of the back portion (18). The height and width of these slots is not critical but should be of sufficient size to permit enhanced flexibility and bending of the elongated neck encircling band (12). Preferably these slots are at least about 2 inches in height and about ¼ inch in width.

The cooperating slits (34) are inscribed into the top and bottom edges of the back portion (18) and extend part of the way into the back portion. The extent of the extension of these slits (34) is not critical although it should not reach the slots (32). The slits (34) preferably are at least about a ½ to 1 inch or so in length. These slots (32) and slits (34) should be arranged in such a manner as to provide adequate flexibility and bendability to the back portion (18) of the elongated neck encircling band (12) without impacting on the structural integrity of the cervical collar (10).

An integral part of the back portion (18) located distal from the frontal portion (16) is the back side portion (20). This back side portion (20) is generally an elongated tab extending from the body of the back portion, and integrally connected to the back portion (18). In an alternative embodiment the back side portion (18) merges into the back portion and is eliminated as a discrete element of the device. A number of elongated slots (36) similar to those contained in the body of the back portion (18) may be provided in this back side portion (20). Distal from the back side portion (20) of the elongated neck encircling band (12) is the front end portion (22) which extends out from the frontal portion (16). It acts in concert with the back side portion (20) when the cervical collar is placed around a user's neck. The frontal end portion (22) is also generally only a tab of generally rectangular shape extending from the body of the frontal portion (16) of the cervical collar. In an alternative embodiment the front end portion (22) merges into the frontal portion (16) and is eliminated as a discrete element of the device. A collar retaining means is added to the elongated encircling band to assist in the securing of the back side portion (20) to the front end portion (22) to hold the improved cervical collar (10) securely in place.

The collar retaining means can be any choice of straps or fasteners which will hold the improved cervical collar (10) together. For example, in a preferred embodiment an elongated hook and loop fastener (40) is secured to the back portion (18) and the back side portion (20) of the cervical collar through selected elongated slots (36) on the back side portion (20) and also the body of the back portion. See FIG. 1A. Corresponding hook and loop fasteners (42) which interact with the hook and loop fasteners strip (40) are secured to the surface of the frontal end portion (22) and the front portion (16) by conventional securing methods, such as adhesives, to permit the hook and loop fasteners strip (40) when encountering the hook and loop fasteners (42) to hold the improved cervical collar (10) securely in place.

The second major element of the cervical collar is the chin support brace. As previously stated, the chin support brace may be a separate element from the elongated neck encircling band or it may be formed as one integral piece of the chin support brace, permanently secured to the elongated neck encircling band. The chin support brace can be a conventional preformed, bowed forward chin support brace or, in an alternative embodiment, the chin support brace can be adjustable and formed from two separate elements.

Figure 3:
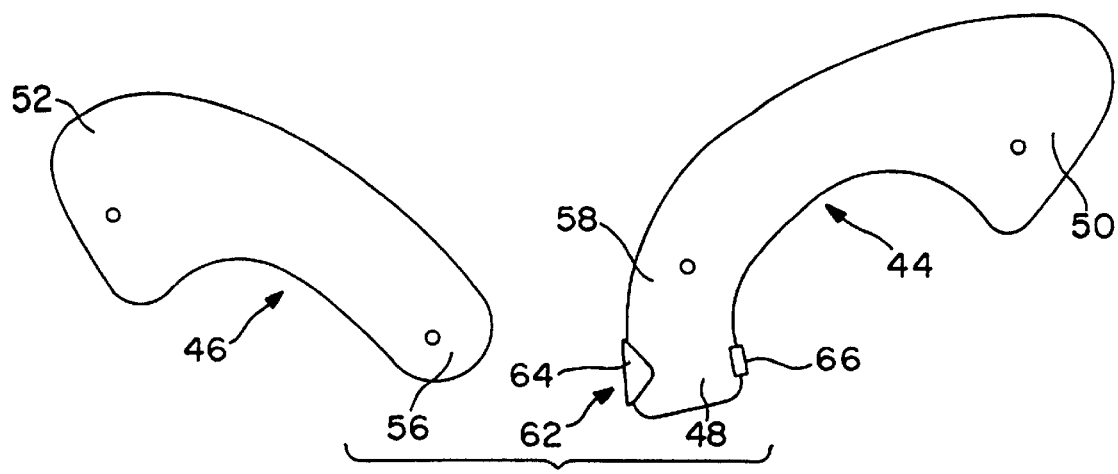
FIG. 3 is an exploded side view of the chin support brace of the cervical collar.

If a two-piece construction is utilized, the two pieces of the chin support brace are a j-shaped element (44) and a curved element (46). See FIG. 3. They are constructed from the same type of stiff plastic material as is the elongated neck encircling band (12). The j-shaped element (44) and the curved element (46) are similar in construction except the j-shaped element has an additional end section (48) which extends the length of the j-shaped element. The second end (50) of the j-shaped element which is distal from the end section (48) and the second end (52) of the curved element (46) are secured at separate locations to the back side of the frontal portion (16) of the elongated neck encircling band. See FIG. 1A. These two second ends are held securely in place by any conventional securing means such as a pin which extends through the surface of the elongated neck encircling band (12) and through the appropriate second ends of the j-shaped element (44) and the curved element (46). They can be permanently secured in place, for example, by rivets or snap fasteners (54).

The curved element (40) and the j-shaped element (44) are also secured to the chin support tab (30) of the frontal portion (16). The first end (56) of the curved element and a portion (58) of the j-shaped element (44), which portion is located close to the end section (48) of the j-shaped element (44), are secured to the chin support tab (30) of the frontal portion (16) of the elongated neck encircling band (12). See FIG. 1A. They are secured to the chin support tab (30) by a securing device (60) similar to the securing devices (54) used to secure the second end (50) of the j-shaped element and the second end (52) of the curved portion to the frontal portion (16). This second securing device (60) may be a pin, rivet or snap fastener. However, whenever a second securing device (60) is chosen, it is required that this second securing device (60) permit rotation of the j-shaped element (44) and curved element (46) about the axis of the second securing device (60) secured to the chin support tab (30).

Figure 4:
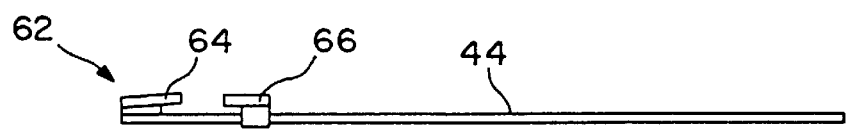
FIG. 4 is a side view of the j-shaped element of the two part chin support brace of the cervical collar.

Secured to the end section (48) of the j-shaped element (44) is the means for holding the chin support brace in a bowed forward position. Any conventional means for locking the two elements in a bowed forward position may be used. Preferably the means for holding is a locking device (62) for locking the two elements of the chin support brace together in a bowed forward position after they are rotated about the axis of the chin support tab (30). See FIG. 3. When each of these elements of the chin support brace are rotated about the axis of the tab, the end section (48) of the j-shaped element (44) rotates upward and forward until its top edge is above the top edge of the curved element (46). As both rotate, the top surface of each of the chin support elements bows forward to provide the support for the chin of the wearer. As these chin support elements are rotated, each side of the frontal end portion (16) will also rotate backward to form the frontal support of the improved cervical collar. After both the j-shaped element (44) and the curved elements (46) are rotated to their bowed forward position, the locking device (62) holds them in this bowed forward position. In a preferred embodiment this locking device (62) is a c-shaped locking device element with a top hook portion (64) and a bottom snap portion (66) which are integral parts of the j-shaped element. See FIGS. 3 and 4. The second end (52) of the curved chin support element hooks under the top hook portion (64) of the c-shaped locking device and above the bottom snap portion (66). The top of the curved chin support slides under the top hook portion (64) of the locking device and snaps in place under the bottom snap portion (66) of the locking device (62) to hold the two piece chin support brace in its bowed forward position. See FIG. 1C.

Figure 5:
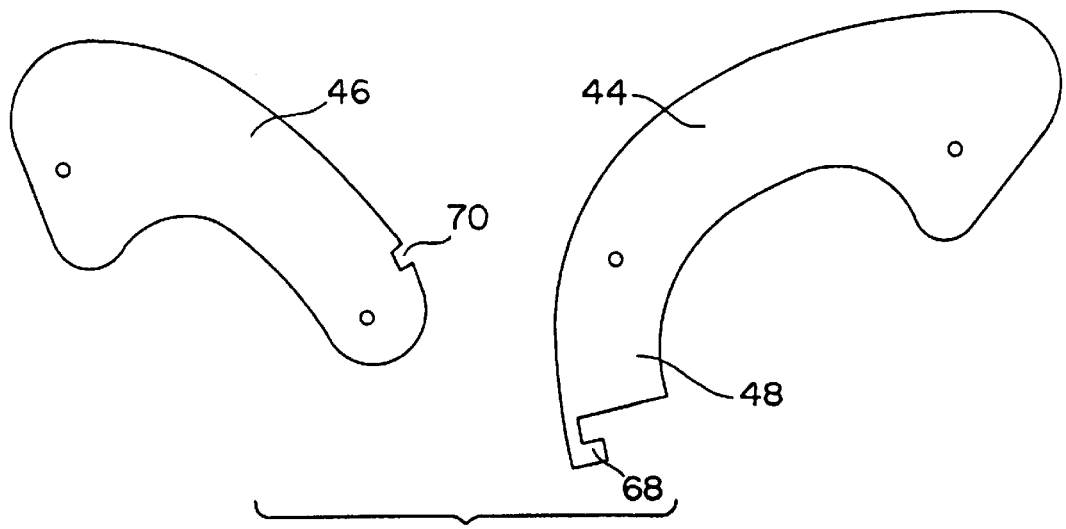
FIG. 5 is a side view of the two part chin support brace of the improved cervical collar with an alternative locking feature.

In an alternative preferred embodiment, the means for holding the chin support brace in a bowed forward position is comprised of a hook and tab piece (68) secured to the j-shaped element (44) which will fit into a slot (70) in the second end of the curved element (46) to hold the chin support elements in their bowed forward position. See FIG. 5.

Figure 1B:
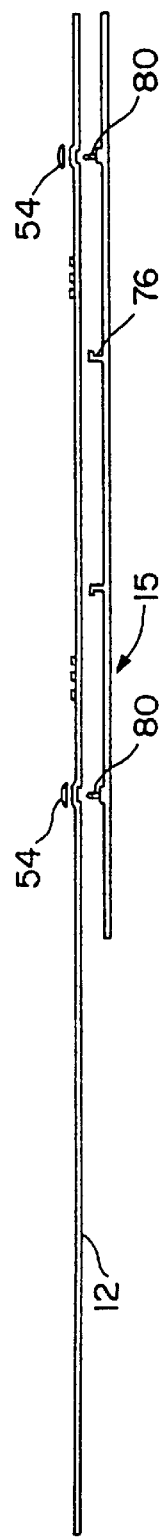

The third element of the cervical collar is the sternum and shoulder brace (15). See FIGS. 6A, 6B and 1. The sternum and shoulder brace is adjustably secured to the frontal portion of the elongated neck encircling band. Its shape is roughly similar to shape of the frontal portion except where the frontal portion forms the cut-out section (26). As previously stated, the lower curved edge (24) of the frontal portion is discontinued at the point where the cut-out section overlaps the larynx. At that same cut-out section (26) the lower curved edge (72) of the sternum and shoulder brace (15) continues in a form roughly parallel with the upper curved edge (28) of the elongated neck encircling band, but located instead at the lower curved edge of the sternum and shoulder brace. In addition, at the location where the upper curved edge of the sternum and shoulder brace meets the cut-out section, the upper curved edge (74) of the sternum and shoulder brace is discontinued. By this design the cut-out section (26) continues uninterrupted from the elongated neck encircling band (28) to the sternum and shoulder brace (15). By this arrangement the cut-out section extends uninterrupted regardless of the adjustment of the height of the sternum and shoulder brace (15) in relation to the elongated neck encircling band (112) thus providing at least one aperture which exposes the neck muscles at the level of the Adam's apple or larynx regardless of adjustment to the height of the sternum and shoulder brace.

Located on each side edge of the cut-out section (26) is a positive alignment tracking means comprised of an overlap section (76) of the sternum and shoulder brace. See FIGS. 1A, 1B, 6A and 6B. This overlap section (76) extends over and around the side edges (78) of the frontal portion of the elongated neck encircling band which form the cut-out section (26). This overlap section (76) is located on each side edge (78) of the cut-out section (26) such that as the sternum and shoulder brace moves vertically upward and downward, the overlap section (76) rests against the side edges (78) of the frontal portion (16) of the elongated neck encircling band (12). As the sternum and shoulder brace is extended downward, the overlap section rests securely against the cut-out section. This arrangement prevents the elongated neck encircling band (12) from twisting out of parallel alignment as the sternum and shoulder brace (15) is extended downward. Any movement by one side of the sternum and shoulder brace downward will automatically result in a corresponding and parallel movement downward on the opposite side of the sternum and shoulder brace (15). By this arrangement it is assured that the sternum and shoulder brace will always extend downward equally on both the left and the right side automatically.

The sternum and shoulder brace (15) is preferably located behind the frontal portion (16) of the elongated encircling band when the cervical collar is viewed from the front. The sternum and shoulder brace (15) is designed to be approximately the same size of the frontal portion (16) and the front end portion (22) of the elongated neck encircling band (12). In particular, when the sternum and shoulder brace is secured behind the frontal portion (16) of the elongated neck encircling band, the sternum and shoulder brace generally does not overlap other sections of the elongated neck encircling band (12). By this arrangement the back portion (18) of the elongated neck encircling band can be placed against the patient's neck and the sternum and shoulder brace (15) can be adjusted without moving the back portion (18) of the elongated neck encircling band (12).

The sternum and shoulder brace (15) slides up and down behind the frontal portion (16) of the elongated neck encircling band on a plurality of posts (80) which ride within slots (82) either in the body of the frontal portion (16) of the elongated encircling band or the body of the sternum and shoulder brace (15) or both. Preferably, a pair of slots (82) is provided on either side of the cut-out section (26) in the sternum and shoulder brace which operate in cooperation with a pair of posts (80) secured to the frontal portion (16) of the elongated neck encircling band on either side of the cut-out section (26). Appropriate rivets and heads for the posts are utilized to hold the sternum and shoulder brace in place while still permitting the sliding movement of the sternum and shoulder brace. In addition, preferably a second pair of vertical slots (84) is provided in the elongated neck encircling band closer to the cut-out section (26) than the first pair of slots. See FIGS. 1A, 6A and 6B. Appropriate posts with rivets and head s operate in conjunction with these slots to permit the sternum and shoulder brace to move vertically in relation to the frontal portion (16) of the elongated neck encircling band. The combination of those four slots and posts operating in conjunction with the overlap sections (76) to permit the sternum and shoulder brace to move smoothly, vertically in relation to the frontal portion (16) of the elongated neck encircling band. By this adjustment mechanism, an appropriate distance between the patient's sternum and shoulder and the underside of the patient's jaw at the chin can be maintained which will effectively support the patient's jaw. By modifying the location of the sternum and shoulder brace (15) as it relates to the elongated neck encircling band (12) on the patient, adequate support for the patient's neck can be achieved.

While the location of the sternum and shoulder brace (15) can be adjusted vertically by this system of slots and posts, it is necessary that the precise location of the sternum and shoulder brace (15) in relation to the frontal portion (16) of the elongated neck encircling band (12) be fixed by a locking mechanism which will prevent the sternum and shoulder brace (15) from collapsing under pressure from the patient. This positive locking system can be any of a number of existing systems. However, preferably, a new ratchet teeth system (86) is utilized to provide this positive locking system. See FIG. 1A.

In one preferred embodiment the ratchet teeth system (86) is designed to permit the sternum and shoulder brace (15) of the cervical collar to be extended downwardly but not to allow it to ascend after its extension. This type of positive locking system is quick to use and provides safety for the patient. In this preferred system, one or preferably a pair of rows of ratchet teeth (88) is secured to the outer surface of the elongated neck encircling band, preferably one of each is located on either side of the second set of slots (84) on the frontal portion (16) of the elongated neck encircling band (12). These rows of ratchet teeth (88) are cut such that a pawl (90) located in a cover piece (92) which covers the ratchet teeth will permit downward movement of the sternum and shoulder brace only. See FIG. 7A. Upward movement of the sternum and shoulder brace (15) is prevented by the interaction of the pawl (90) with the ratchet teeth. The cover piece (92) which covers and holds the pawl can be any conventional design such that it will move in relation to the ratchet teeth in line with the movement of the sternum and shoulder brace itself. In one embodiment the cover piece is secured at its top portion to the sternum and shoulder brace as an element of the post which passes through the slot (84) and at its bottom portion by a second post with rivet and hook secured to the sternum and shoulder brace. Various other arrangements can be conceived all within the confines of the instant invention. Preferably, the pawl (90) will be located within a slot (96) in the cover piece (92). See FIGS. 8A and 8B. As the cover piece (92) moves vertically in relation to the first set of ratchet teeth (88), this allows the pawl (90) to move vertically in relation to the first set of ratchet teeth (88). This permits the teeth (98) of the pawl to slide over the first set of ratchet teeth (88) interacting therewith.

As an improvement on this system the pawl (90) can be located on a separate slide piece (100) slidably secured within the cover piece (92) such that the pawl (90) may be pulled out of line with the first set of ratchet teeth (88), thus permitting the sternum and shoulder brace (15) to move upward as well as downward. See FIG. 9. Preferably, the slide piece (100) is engaged in a system which will lock the teeth of the pawl in place preventing vertical movement of the sternum and shoulder brace (15) after the sternum and shoulder brace has been secured to the patient but which can be slidably adjusted to permit the movement of the sternum and shoulder brace upward after it is removed from the patient.

As a further improvement upon this system a second group of ratchet teeth (102) is cut into the surface of the frontal portion (16) of the elongated neck encircling band (12) running in a row parallel to the first set of ratchet teeth rows (88) previously discussed. See FIG. 1A and FIGS. 7A, 7B and 7C. The direction of the cut of this second row of ratchet teeth (102) is reversed from the cut of the previously discussed ratchet teeth. This second group of ratchet teeth (102) are angled in the opposite direction from the first set of ratchet teeth. With this arrangement the cover piece (92) also contains a second pawl (104), the direction of the cut of the teeth of which is also reversed from that of the first pawl (90). This second pawl (104) is movable so that it can be moved into and out of alignment with the second set of ratchet teeth (102). Thus, when the second pawl (104) and the second set of ratchet teeth (102) are aligned, movement of the sternum and shoulder brace is prevented in the direction opposite from the movement prevented by the first set of ratchet teeth (88) and first pawl (90). See FIG. 7B. Preferably, when this second set of ratchet teeth (102) and second pawl (104) are engaged, they will prevent the sternum and shoulder brace from being further extended downward. If the first set of ratchet teeth (88) and the first pawl (90) are also engaged, this arrangement provides a complete locking system for the sternum and shoulder brace, thus preventing not only retrograde movement vertically but also additional movement downward of the sternum and shoulder brace. See FIG. 7C.

Figure 7A:
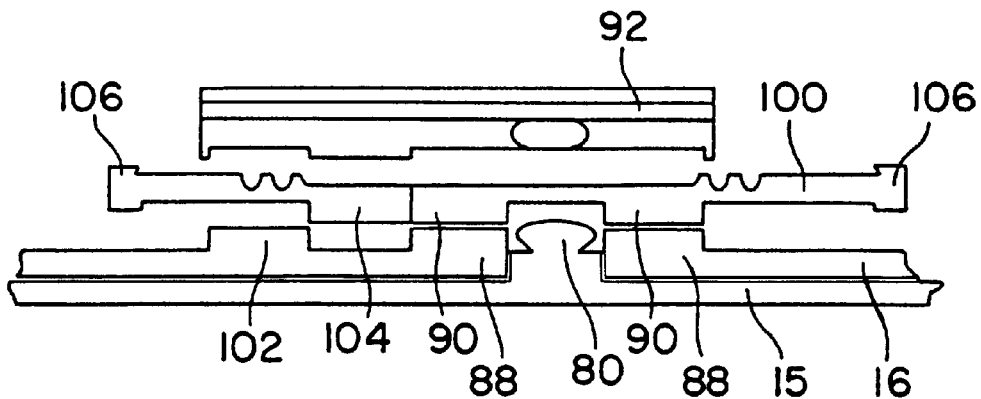
FIG. 7A is an edge view of the locking mechanism showing the ratchet teeth and pawl system where downward movement of the sternum and shoulder brace is permitted.
Figure 7B:
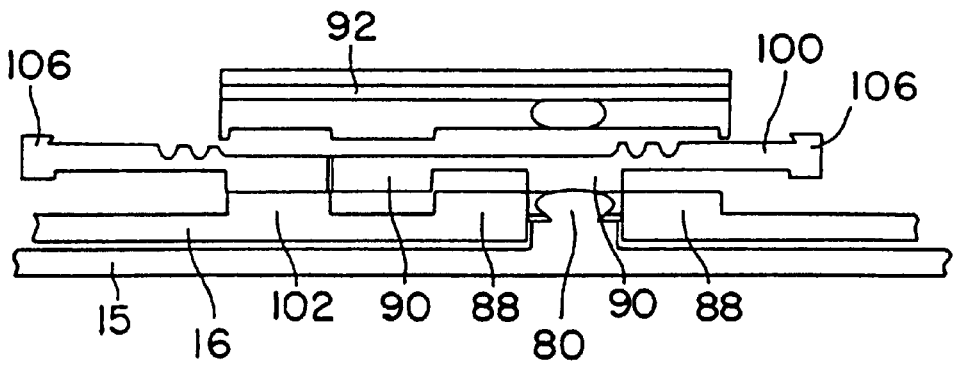
FIG. 7B is an edge view of the locking mechanism showing the ratchet teeth and pawl system where upward movement of the sternum and shoulder brace is permitted.
Figure 7C:
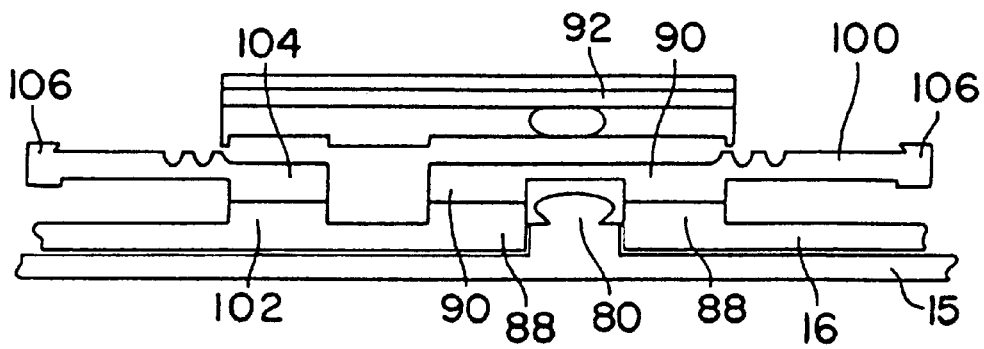
FIG. 7C is an edge view of the locking mechanism showing the ratchet teeth and pawl system where no movement of the sternum and shoulder brace is permitted.

In this alternative embodiment it is critical that both sets of pawls (90, 104) be moveable horizontally so that each pawl can not only be engaged with the appropriate ratchet teeth to prevent movement in one direction but that each pawl can be moved horizontally out of alignment with the corresponding ratchet teeth to permit appropriate vertical movement of the sternum and shoulder brace. By having the pawls independently moveable in a horizontal direction within the cover piece (92), the greatest degree of adjustment capacity for the sternum and shoulder brace is provided while at the same time providing a positive locking of the sternum and shoulder brace in place. The alternative arrangements are shown in FIGS. 7A, 7B and 7C. In FIG. 7A the first set of ratchet teeth rows (88) are lined up with the first pawl (90). With this arrangement of the pawl and ratchet teeth, the sternum and shoulder brace (15) can be extended downward moving the sternum and shoulder brace closer to the patient's chest. Retrograde movement upward is prevented by the interaction of the first set of ratchet teeth (88) and the first pawl (90). In this embodiment the second pawl and the second set of ratchet teeth (102) are not in alignment. Once the correct position of the sternum and shoulder brace is achieved for the patient, the second pawl (104) is moved in a horizontal direction until it is in alignment with the second set of ratchet teeth (102). See FIG. 7C. At this point the sternum and shoulder brace can neither move further downward nor can it move upward. Moving the first pawl (90) out of alignment with the first set of ratchet teeth rows (88) will permit the sternum and shoulder brace to be retracted upward. See FIG. 7B. Once the precise location for the sternum and shoulder brace (15) in relation the frontal portion (16) of the elongated neck encircling band is achieved, both pawls are placed in alignment with their respective ratchet teeth thus preventing any further movement of the sternum and shoulder brace. See FIG. 7C.

Preferably the set of pawls are arranged in a positive locking system such that they will be locked in alignment with the respective ratchet teeth. In one embodiment of this system, each set of pawls (90, 104) has attached to its outside edge a tab system which will assist in locking the pawls into a predetermined height after final adjustment of the location of the sternum and shoulder brace of the cervical collar. A number of different tab systems can be utilized. In one preferred embodiment, the outside end of each pawl attaches to a tab (106) which is rotatably over the cover piece (92) and locks in place to the top surface of the cover piece. When properly designed, these tabs will only lock in position to the cover piece when the sternum and shoulder brace may move neither upward nor downward. In this embodiment, both sets of pawls will engage both sets of ratchet teeth rows to lock the sternum and shoulder brace (15) securely in place. Other systems can be designed which will lock the cooperating pawls and ratchet teeth in place, all of which are covered by this invention.

In the preferred system, a pair of ratchet teeth rows run vertically on both sides of one of the slots. Within this slot is the post which holds the cover piece (92) over the locking system and which is secured to the back side of the sternum and shoulder brace. Preferably the two sets of ratchet teeth rows are located one on either side of the slot (84). These ratchet teeth (88), when operating with the corresponding pawl (90), permit the sternum and shoulder brace to extend downward but do not permit it to move back upward. A third row of ratchet teeth (102) is located outside of the first two rows of ratchet teeth away from the cut-out section (26). These ratchet teeth are cut with the opposite angle from the teeth in the first two rows. This third row of ratchet teeth (102) when operating in conjunction with a cooperating reverse pawl (104) prevent further extension of the sternum and shoulder brace downward from the elongated neck encircling band. See FIG. 1A.

Figure 10:
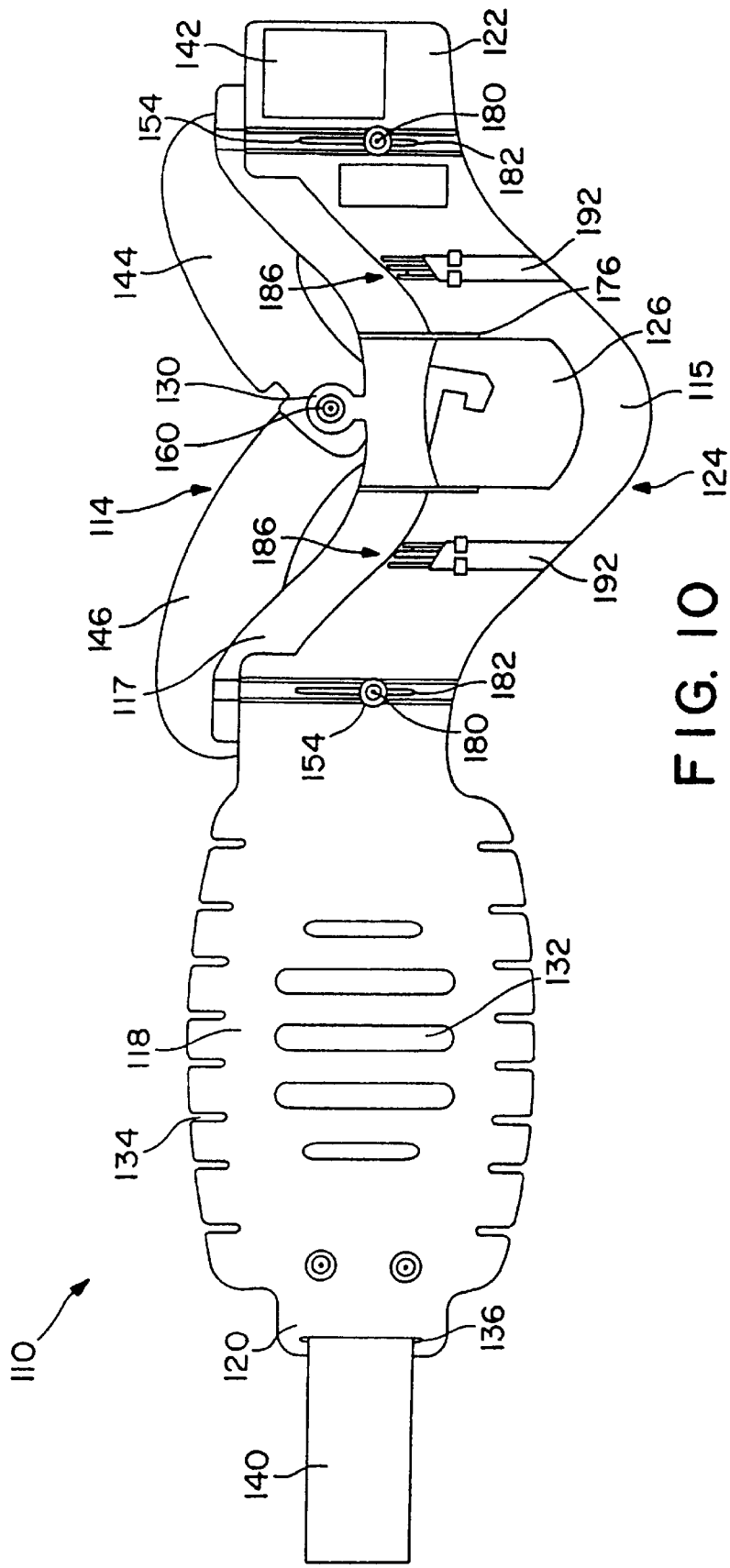
FIG. 10 is a front plan view of an alternative embodiment of the cervical collar in its flat position.

In an alternative embodiment an alternative improved cervical collar (110) is comprised of an elongated neck encircling band (112) containing as an integral element thereof a sternum and shoulder brace (115), a chin support height adjustment piece (117) and a chin support brace (114) with an adjustment system for adjusting the height of the chin support brace in relation to the elongated neck encircling band (112). See FIG. 10.

The elongated neck encircling band (112) is formed from a stiff, plastic sheet material such as high density polyethylene, polyvinyl chloride or other such stiff, sturdy plastic material. The elements of the cervical collar may be die cut, extruded or prepared from molds as is conventional in the industry. For comfort there may be secured to the inner surface of this stiff plastic at various locations soft, foam type pads (not shown) which are comprised of conventional soft plastic material. These soft plastic pads are secured to the stiff plastic material by any conventional securing means such as an adhesive or snap fasteners. It is preferred that these foam pads be secured by cement or other adhesive to reduce the number of parts of the cervical collar (110).

The elongated neck encircling band (12) is preferably of one-piece construction generally comprised of a sternum and shoulder brace (115), a back portion (118), a back side portion (120) and a front end portion (122). See FIGS. 11A and 11B. The elongated neck encircling band (112) is asymmetrical in design.

The sternum and shoulder brace (115) when placed flat is generally curvilinear in design, curving downward and then generally curving back upward from the front end portion (122) to the back portion (118) with an opposite longitudinal curved edge which runs from one side of the frontal portion to the other side. See FIG. 11A. The upper curved edge (128) of the sternum and shoulder brace is discontinued at that point where a cut-out section (126), which in use overlaps the Adam's apple or larynx of the wearer is formed, to permit a tracheotomy to be performed through the cut-out section (126) with the cervical collar (110) in place. The lower curved edge (124) of the sternum and shoulder brace (115) runs roughly parallel to the upper curved edge (128) except that it is not discontinued as with the upper curved edge (128).

Secured to one side of the chin support height adjustment piece (117) and an integral part of the cervical collar is the back portion (118) of the cervical collar (110). The back portion (118) can be of any conventional shape from generally rectangle to generally oval. The back portion (118) of the elongated neck encircling band (112) contains a number of vertical elongated slots (132) and cooperating slits (134) to make the neck encircling band (112) more flexible. These slots (132) are generally cut-out sections contained in the body of the back portion (118) running horizontally from near where the sternum and shoulder brace (115) joins the back portion (118) to the opposite side of the back portion. These slots (132) are generally located in the body of the back portion (118) running approximately half way the distance between the top and the bottom of the back portion (118). The height and width of these slots is not critical but should be of sufficient size to permit enhanced flexibility and bending of the elongated neck encircling band (112). Preferably these slots are at least about 2 inches in height and about ¼ inch in width.

The cooperating slits (134) are inscribed into the top and bottom edges of the back portion (118) and extend part of the way into the back portion. The extent of the extension of these slits (134) is not critical although it should not reach the slots (132). The slits (134) preferably are at least about a ½ to 1 inch or so in length. These slots (132) and slits (134) should be arranged in such a manner as to provide adequate flexibility and bendability to the back portion (118) of the elongated neck encircling band (112) without impacting on the structural integrity of the cervical collar (110).

An integral part of the back portion (118) located distal from the sternum and shoulder brace (115) is the back side portion (120). This back side portion (120) is generally an elongated tab extending from the body of the back portion, and integrally connected to the back portion (118). In an alternative embodiment the back side portion (118) merges into the back portion and is eliminated as a discrete element of the device. A number of elongated slots (136) similar to those contained in the body of the back portion (118) may be provided in this back side portion (120). Distal from the back side portion (120) of the elongated neck encircling band (112) is the front end portion (122) which extends out from the sternum and shoulder brace (115). It acts in concert with the back side portion (120) when the cervical collar is placed around a user's neck. The frontal end portion (122) is also generally only a tab of generally rectangular shape extending from the sternum and shoulder brace (115) of the cervical collar. In an alternative embodiment the front end portion (122) merges into the sternum and shoulder brace (115) and is eliminated as a discrete element of the device. A collar retaining means is added to the elongated encircling band to assist in the securing of the back side portion (120)

to the front end portion (122) to hold the improved cervical collar (110) securely in place.

The collar retaining means can be any choice of straps or fasteners which will hold the improved cervical collar (110) together. For example, in a preferred embodiment an elongated hook and loop fastener (140) is secured to the back portion (118) and the back side portion (120) of the cervical collar through selected elongated slots (136) on the back side portion (120) and also the body of the back portion. See FIG. 10. Corresponding hook and loop fasteners (142) which interact with the hook and loop fasteners strip (140) are secured to the surface of the frontal end portion (122) and the sternum and shoulder brace (115) by conventional securing methods, such as adhesives, to permit the hook and loop fasteners strip (140) when encountering the hook and loop fasteners (142) to hold the improved cervical collar (110) securely in place.

The sternum and shoulder brace (115) is an integral part of the elongated neck encircling band (112). The shape of the sternum and shoulder brace is roughly similar in shape of the chin support height adjustment piece (117) except where the sternum and shoulder brace forms the cut-out section (126). The upper curved edge (128) of the sternum and shoulder brace (115) is discontinued at the point where the cut-out section (126) overlaps the larynx. At that same cut-out section (126) the upper curved edge (172) of the chin support height adjustment piece (117) continues in a form roughly parallel with the lower curved edge (124) of the sternum and shoulder brace (115). In addition, at the location where the lower curved edge of the chin support height adjustment piece (117) meets the cut-out section, the lower curved edge (174) of the chin support height adjustment piece (117) is discontinued. By this design the cut-out section (126) continues uninterrupted from the chin support height adjustment piece (117) to the sternum and shoulder brace (115). By this arrangement the cut-out section extends uninterrupted regardless of the adjustment of the height of the sternum and shoulder brace (115) in relation to the chin support height adjustment piece (117) thus providing at least one aperture which exposes the neck muscles at the level of the Adam's apple or larynx regardless of the adjustment to the height of the sternum and shoulder brace.

Located on each side edge of the cut-out section (126) is a positive alignment tracking means comprised of an overlap section (176) of the chin support height adjustment piece (117). See FIGS. 10 and 12A. This overlap section (176) extends over and around the side edges (178) of the sternum and shoulder brace (115) of the elongated neck encircling band which form the cut-out section (126). This overlap section (176) is located on each side edge (178) of the cut-out section (126) such that as the chin support height adjustment piece (117) moves vertically upward and downward, the overlap section (176) rests against the side edges (178) of the sternum and shoulder brace (115). As the sternum and shoulder brace is extended downward, the overlap section (176) rests securely against the cut-out section. This arrangement prevents the sternum and shoulder brace (115) from twisting out of parallel alignment as the chin support height adjustment piece (117) is extended upward. Any movement by one side of the sternum and shoulder brace downward will automatically result in a corresponding and parallel movement downward on the opposite side of the sternum and shoulder brace (115). By this arrangement it is assured that the sternum and shoulder brace will always extend downward equally on both the left and the right side automatically.

Located behind the sternum and shoulder brace (115) of the elongated encircling band when the cervical collar is viewed from the front is the chin support height adjustment piece (117). The chin support height adjustment piece (117) is designed to be approximately the same size as the combined sternum and shoulder brace (115) and the front end portion (122) of the elongated neck encircling band (112). The chin support height adjustment piece (117) has an upper curvilinear edge (172) which runs approximately parallel to the upper curved edge (128) of the sternum and shoulder brace. In addition, the lower curved edge (174) of the chin support height adjustment piece runs approximately parallel to the lower curved edge (124) of the sternum and shoulder brace. As previously stated, at the point where the lower curved edge (174) of the chin support height adjustment piece meets the cut-out section (126) the lower curved edge is discontinued. Thus, the cut-out section (126) extends uninterrupted regardless of the adjustment of the height of the sternum and shoulder brace (115) in relation to the chin support height adjustment piece (117), thus providing at least one aperture which exposes the neck muscles at the level of the Adam's apple or larynx regardless of the adjustment to the height of the sternum and shoulder brace.

Secured to the upper curved edge (172) of the chin support height adjustment piece (117) is a chin support tab (130) extending upward away from the upper curved edge (172). This chin support tab (130) is used to secure the chin support brace (114) to the chin support height adjustment piece (117). See FIGS. 10 and 12A.

The chin support height adjustment piece (117) slides up and down behind the sternum and shoulder brace (115) of the elongated neck encircling band on a plurality of posts (180) which ride within slots (182) either in the body of the sternum and shoulder brace (115) of the elongated encircling band or the body of the chin support height adjustment piece (117) or both. Preferably, a pair of slots (182) are provided on either side of the cut-out section (126) in the sternum and shoulder brace (115) which operate in cooperation with a pair of posts (180) slidably secured to the sternum and shoulder brace (115) of the elongated neck encircling band on either side of the cut-out section (126). Appropriate rivets and heads for the posts are utilized to hold the chin support height adjustment piece (117) in place while still permitting the sliding movement of the sternum and shoulder brace (115). In addition, preferably a second pair of vertical slots (184) is provided in the sternum and shoulder brace (115) closer to the cut-out section (126) than the first pair of slots. See FIGS. 10 and 11A. Appropriate posts with rivets and heads operate in conjunction with these slots to permit the chin support height adjustment piece (117) to move vertically in relation to the sternum and shoulder brace (115) of the elongated neck encircling band. The combination of those four slots and posts operating in conjunction with the overlap sections (176) to permit the chin support height adjustment piece to move smoothly, vertically in relation to the sternum and shoulder brace of the elongated neck encircling band. By this adjustment mechanism, an appropriate distance between the patient's sternum and shoulder and the underside of the patient's jaw at the chin can be maintained which will effectively support the patient's jaw. By modifying the location of the chin support height adjustment piece (117) on the patient as it relates to the elongated neck encircling band (112), adequate support for the patient's neck can be achieved.

While the location of the sternum and shoulder brace (115) can be adjusted vertically by this system of slots and posts, it is necessary that the precise location of the sternum and shoulder brace (115) in relation to the chin support height adjustment piece (117) be fixed by a locking mechanism which will prevent the sternum and shoulder brace (115) from collapsing under pressure from the patient. This positive locking system can be any of a number of existing systems. However, preferably, a new ratchet teeth system (186) is utilized to provide this positive locking system. See FIGS. 10, 16A, 16B and 16C.

In one preferred embodiment the ratchet teeth system (186) is designed to permit the sternum and shoulder brace (115) of the cervical collar to be extended downwardly but not to allow it to ascend after its extension. This type of positive locking system is quick to use and provides safety for the patient. In this preferred system, one or preferably a pair of rows of ratchet teeth (188) are secured to the outer surface of the elongated neck encircling band, preferable one of each is located on either side of the second set of slots (184) on the sternum and shoulder brace (115) of the elongated neck encircling band (112). These rows of ratchet teeth (188) are cut such that a pawl (190) located in a cover piece (192) which covers the ratchet teeth will permit downward movement of the sternum and shoulder brace only. See FIGS. 10 and 16A. Upward movement of the sternum and shoulder brace (115) is prevented by the interaction of the pawl (190) with the ratchet teeth. The cover piece (192) which covers and holds the pawl can be any conventional design such that it will move in relation to the ratchet teeth in line with the movement of the sternum and shoulder brace itself. In one embodiment the top portion of the cover piece is secured to the chin support height adjustment piece (117) as an element of the post which passes through the slot (184) and at its bottom portion by a second post with rivet and hook secured to the chin support height adjustment piece. Various other arrangements can be conceived all within the confines of the instant invention. Preferably, the pawl (190) will be located within a slot (196) in the cover piece (192). See FIGS. 16A, 16B, 16C, 17A and 17B. As the cover piece (192) moves vertically in relation to the first set of ratchet teeth (188), this allows the pawl (190) to move vertically in relation to the first set of ratchet teeth (188). This permits the teeth (198) of the pawl to slide over the first set of ratchet teeth (188) interacting therewith.

As an improvement on this system the pawl (190) can be located on a separate slide piece (200) slidably secured within the cover piece (192) such that the pawl (190) may be pulled out of line with the first set of ratchet teeth (188), thus permitting the sternum and shoulder brace (115) to move upward as well as downward. See FIGS. 16A, 16B, 16C and 18. Preferably, the slide piece (200) is engaged in a system which will lock the teeth of the pawl in place preventing vertical movement of the sternum and shoulder brace (115) after the sternum and shoulder brace has been secured to the patient but which can be slidably adjusted to permit the movement of the sternum and shoulder brace upward after it is removed from the patient.

As a further improvement upon this system a second group of ratchet teeth (202) is cut into the surface of the elongated neck encircling band (112) running in a row parallel to the first set of ratchet teeth rows (188) previously discussed. See FIGS. 10 and 11A. The direction of the cut of this second row of ratchet teeth (202) is reversed from the cut of the previously discussed ratchet teeth. This second group of ratchet teeth (202) are angled in the opposite direction from the first set of ratchet teeth. With this arrangement the cover piece (192) also contains a second pawl (204), the direction of the cut of the teeth of which is also reversed from that of the first pawl (190). This second pawl (204) is movable so that it can be moved into and out of alignment with the second set of ratchet teeth (202). Thus, when the second pawl (204) and the second set of ratchet teeth (202) are aligned, movement of the sternum and shoulder brace is prevented in the direction opposite from the movement prevented by the first set of ratchet teeth (188) and first pawl (190). See FIG. 16B. Preferably, when this second set of ratchet teeth (202) and second pawl (204) are engaged, they will prevent the sternum and shoulder brace from being further extended downward. If the first set of ratchet teeth (188) and the first pawl (190) are also engaged, this arrangement provides a complete locking system for the sternum and shoulder brace, thus preventing not only retrograde movement vertically but also additional movement downward of the sternum and shoulder brace. See FIG. 16C.

Figure 16A:
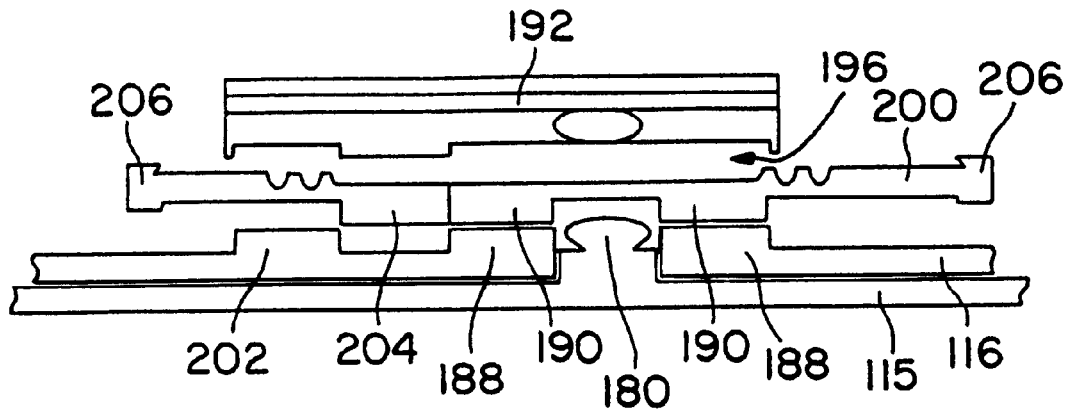
FIG. 16A is an edge view of the alternative embodiment of the locking mechanism showing the ratchet teeth and pawl system where downward movement of the sternum and shoulder brace is permitted.
Figure 16B:
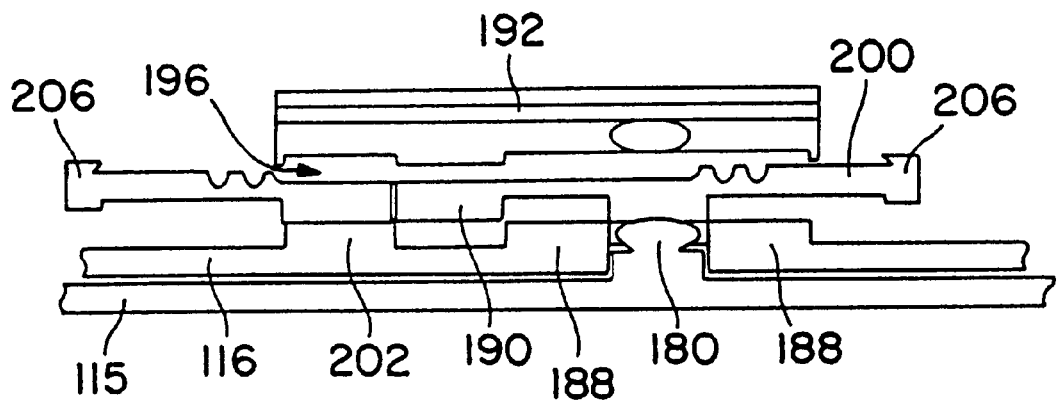
FIG. 16B is an edge view of the alternative embodiment of the locking mechanism showing the ratchet teeth and pawl system where upward movement of the sternum and shoulder brace is permitted.
Figure 16C:
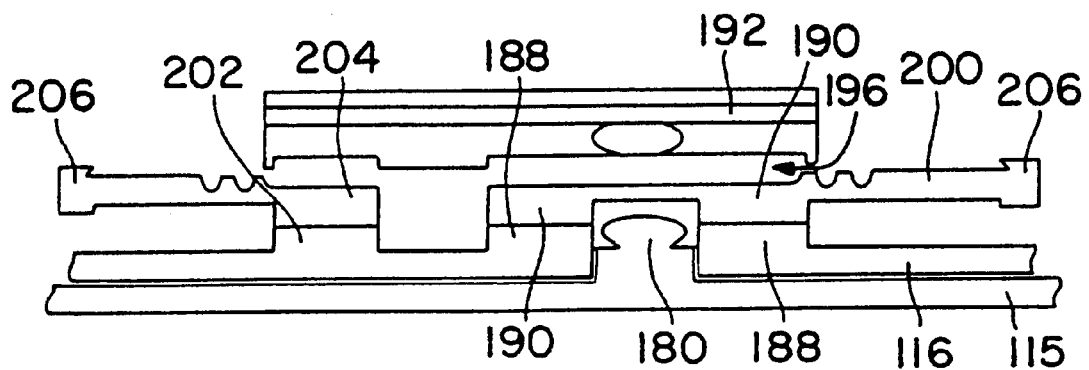
FIG. 16C is an edge view of the alternative embodiment of the locking mechanism showing the ratchet teeth and pawl system where no movement of the sternum and shoulder brace is permitted.

In this alternative embodiment it is critical that both sets of pawls (190, 204) be moveable horizontally so that each pawl can not only be engaged with the appropriate ratchet teeth to prevent movement in one direction but that each pawl can be moved horizontally out of alignment with the corresponding ratchet teeth to permit appropriate vertical movement of the sternum and shoulder brace. By having the pawls independently moveable in a horizontal direction within the cover piece (192), the greatest degree of adjustment capacity for the sternum and shoulder brace is provided while at the same time providing a positive locking of the sternum and shoulder brace in place. The alternative arrangements are shown in FIGS. 16A, 16B and 16C. In FIG. 16A the first set of ratchet teeth rows (188) are lined up with the first pawl (190). With this arrangement of the pawl and ratchet teeth, the sternum and shoulder brace (115) can be extended downward moving the sternum and shoulder brace closer to the patient's chest. Retrograde movement upward is prevented by the interaction of the first set of ratchet teeth (188) and the first pawl (190). In this embodiment the second pawl and the second set of ratchet teeth (202) are not in alignment. Once the correct position of the sternum and shoulder brace is achieved for the patient, the second pawl (204) is moved in a horizontal direction until it is in alignment with the second set of ratchet teeth (202). See FIG. 16C. At this point the sternum and shoulder brace can neither move further downward nor can it move upward. Moving the first pawl (190) out of alignment with the first set of ratchet teeth rows (188) will permit the sternum and shoulder brace to be retracted upward. See FIG. 16B. Once the precise location for the sternum and shoulder brace (115) in relation the chin support height adjustment piece (117) is achieved, both pawls are placed in alignment with their respective ratchet teeth thus preventing any further movement of the sternum and shoulder brace. See FIG. 16C.

Preferably the set of pawls are arranged in a positive locking system such that they will be locked in alignment with the respective ratchet teeth. In one embodiment of this system, each set of pawls (190, 204) has attached to its outside edge a tab system which will assist in locking the pawls into a predetermined height after final adjustment of the location of the sternum and shoulder brace of the cervical collar. A number of different tab systems can be utilized. In one preferred embodiment, the outside end of each pawl attaches to a tab (206) which is rotatably over the cover piece (192) and locks in place to the top surface of the cover piece. When properly designed, these tabs will only lock in position to the cover piece when the sternum and shoulder brace may move neither upward nor downward. In this embodiment, both sets of pawls will engage both sets of ratchet teeth rows to lock the sternum and shoulder brace (115) securely in place. Other systems can be designed which will lock the cooperating pawls and ratchet teeth in place, all of which are covered by this invention.

In the preferred system, a pair of ratchet teeth rows run vertically on both sides of one of the slots. Within this slot is the post which holds the cover piece (192) over the locking system and which is secured to the back side of the chin support height adjustment piece (117). Preferably the two sets of ratchet teeth rows are located one on either side of the slot (184). These ratchet teeth (188), when operating with the corresponding pawl (190), permit the sternum and shoulder brace to extend downward but do not permit it to move back upward. A third row of ratchet teeth (202) is located outside of the first two rows of ratchet teeth away from the cut-out section (126). These ratchet teeth are cut with the opposite angle from the teeth in the first two rows. This third row of ratchet teeth (202) when operating in conjunction with a cooperating reverse pawl (204) prevent further extension of the sternum and shoulder brace downward from the elongated neck encircling band.

The third major element of the cervical collar is the chin support brace. As previously stated, the chin support brace may be a separate element from the chin support height adjustment piece (117) or it may be formed as one integral piece permanently secured to the chin support height adjustment piece. The chin support brace can be a conventional preformed, bowed forward chin support brace or, in an alternative embodiment, the chin support brace can be adjustable and formed from two separate elements.

Figure 13:
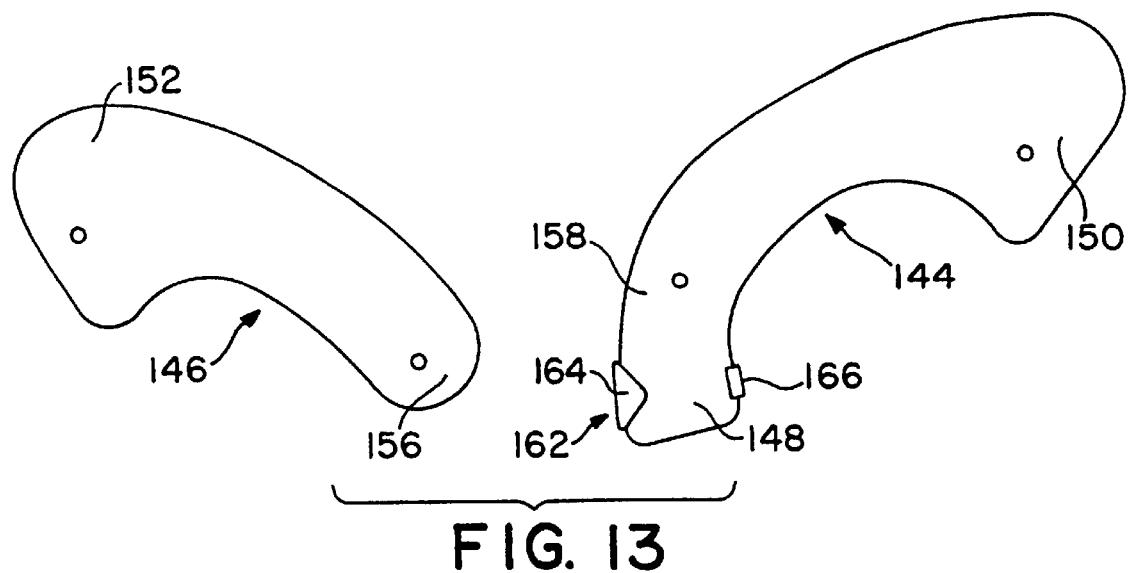
FIG. 13 is an exploded side view of one embodiment of the chin support brace of the alternative embodiment of the cervical collar.

If a two-piece construction is utilized, the two pieces of the chin support brace are a j-shaped element (144) and a curved element (146). See FIG. 13. They are constructed from the same type of stiff plastic material as is the elongated neck encircling band (112). The j-shaped element (144) and the curved element (146) are similar in construction except the j-shaped element has an additional end section (148) which extends the length of the j-shaped element. The second end (150) of the j-shaped element which is distal from the end section (148) and the second end (152) of the curved element (146) are secured at separate locations to the back side of the chin support height adjustment piece (117). See FIG. 10. These two second ends are held securely in place by any conventional securing means such as a pin which extends through the surface of the chin support height adjustment piece (117) and through the appropriate second ends of the j-shaped element (144) and the curved element (146). They can be permanently secured in place, for example, by rivets or snap fasteners (154).

The curved element (140) and the j-shaped element (144) are also secured to the chin support tab (130) of the chin support height adjustment piece (117). The first end (156) of the curved element and a portion (158) of the j-shaped element (144), which portion is located close to the end section (148) of the j-shaped element (144), are secured to the chin support tab (130) of the chin support height adjustment piece (117). See FIG. 10. They are secured to the chin support tab (130) by a securing device (160) similar to the securing devices (154) used to secure the second end (150) of the j-shaped element and the second end (152) of the curved portion to the chin support height adjustment piece (117). This second securing device (160) may be a pin, rivet or snap fastener. However, whenever a second securing device (160) is chosen, it is required that this second securing device (160) permit rotation of the j-shaped element (144) and curved element (146) about the axis of the second securing device (160) secured to the chin support tab (130).

Figure 14:
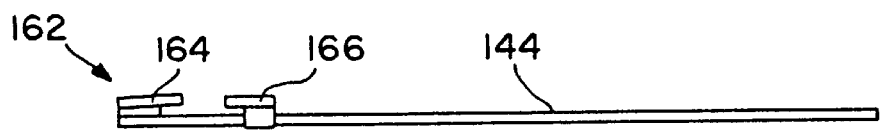
FIG. 14 is a side view of the j-shaped element of the two part chin support brace of the alternative embodiment of the cervical collar.

Secured to the end section (148) of the j-shaped element (144) is the means for holding the chin support brace in a bowed forward position. Any conventional means for locking the two elements in a bowed forward position may be used. Preferably the means for holding is a locking device (162) for locking the two elements of the chin support brace together in a bowed forward position after they are rotated about the axis of the chin support tab (130). See FIG. 13. When each of these elements of the chin support brace are rotated about the axis of the tab, the end section (148) of the j-shaped element (144) rotates upward and forward until its top edge is above the top edge of the curved element (146). As both rotate, the top surface of each of the chin support elements bows forward to provide the support for the chin of the wearer. As these chin support elements are rotated, each side of the chin support height adjustment piece (117) will also rotate backward to form the frontal support of the improved cervical collar. After both the j-shaped element (144) and the curved elements (146) are rotated to their bowed forward position, the locking device (162) holds them in this bowed forward position. In a preferred embodiment this locking device (162) is a c-shaped locking device element with a top hook portion (164) and a bottom snap portion (166) which are integral parts of the j-shaped element. See FIGS. 13 and 14. The second end (152) of the curved chin support element hooks under the top hook portion (164) of the c-shaped locking device and above the bottom snap portion (166). The top of the curved chin support slides under the top hook portion (164) of the locking device and snaps in place under the bottom snap portion (166) of the locking device (162) to hold the two piece chin support brace in its bowed forward position.

Figure 15:
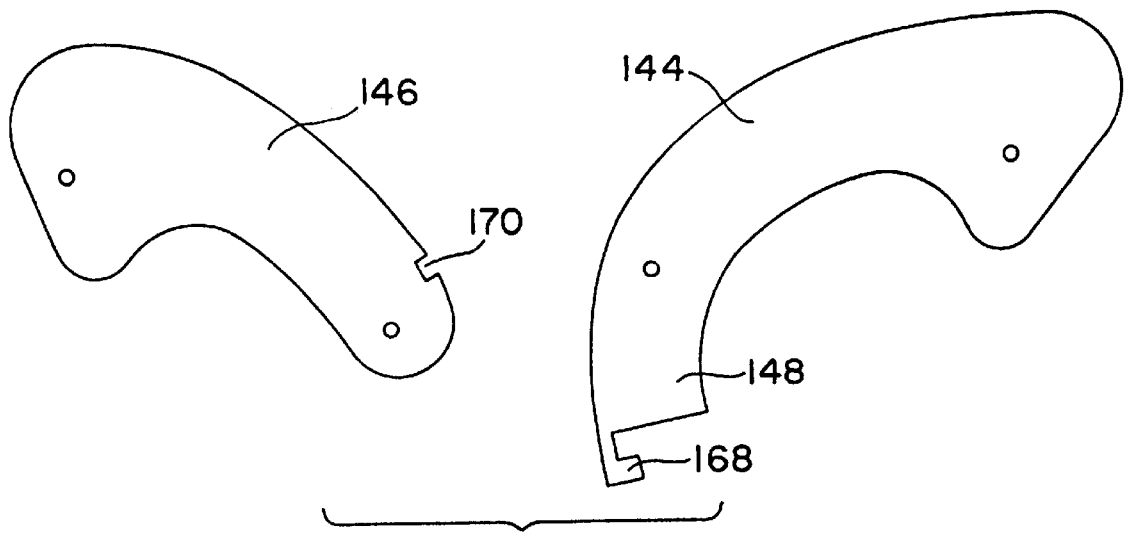
FIG. 15 is a side view of the two part chin support brace of the alternative embodiment of the improved cervical collar with an alternative locking feature.

In an alternative preferred embodiment, the means for holding the chin support brace in a bowed forward position is comprised of a hook and tab piece (168) secured to the j-shaped element (144) which will fit into a slot (170) in the second end of the curved element (146) to hold the chin support elements in their bowed forward position. See FIG. 15.

In operation, when the first embodiment of the cervical collar is to be used, the back portion (18) of the elongated neck encircling band is wrapped around the back of the patient's neck. The frontal portion (16) is held in place against the patient's neck and chest. The collar retaining element such, as an elongated hook and loop fastener (40) which is attached to the back side portion (20), is secured firmly in place against one or more hook and loop fasteners (42) which are secured to the frontal end portion (22) and, if necessary, on the top surface of the frontal portion of the elongated neck encircling band. If the cervical collar does not have a two-piece adjustable chin support, a single piece chin support is placed against the patient's neck. If a two-piece adjustable chin support is an element, the various elements of the curved chin support are rotated and formed into a bowed forward position using the appropriate locking systems. This results in the chin support brace being bowed forward to more easily support the wearer's chin. The respective pawls (90, 104) are slid to a position which permits the sternum and shoulder brace to be pulled downward until it is firmly in place against the patient's sternum. If a single set of ratchet teeth rows (88) and pawl (90) are present, no further operation is necessary. However, if a reverse ratchet teeth (102) and reverse pawl (104) is present, the tab (106) secured to the reverse pawl is pulled such that the reverse pawl (104) and the row of reverse ratchet teeth (102) interact, thus preventing further downward movement of the sternum and shoulder brace. Tabs (106) connected to both pawls are then locked in place against the cover piece (92). By this mechanism additional upward or additional downward movement of the sternum and shoulder brace is prevented. After the user no longer needs the cervical collar, the hook and loop material strip used as a collar retaining element is removed from the fasteners attached to the frontal portion and the frontal end portion. This removes the cervical collar from the patient's neck.

In operation in the alternative embodiment, when the cervical collar is to be used, the back portion (118) of the elongated neck encircling band is wrapped around the back of the patient's neck. The sternum and shoulder brace (115) is held in place against the patient's chest. The collar retaining element such, as an elongated hook and loop fastener (140) which is attached to the back side portion (120), is secured firmly in place against one or more hook and loop fasteners (142) which are secured to the frontal end portion (122) and, if necessary, on the top surface of the frontal portion of the elongated neck encircling band. If the cervical collar does not have a two-piece adjustable chin support, a single piece chin support is placed against the patient's neck. If a two-piece adjustable chin support is an element, the various elements of the curved chin support are rotated and formed into a bowed forward position using the appropriate locking systems. This results in the chin support brace being bowed forward to more easily support the wearer's chin. The respective pawls (190, 204) are slid to a position which permits the chin support brace (114) secured to the chin support height adjustment piece (117) to be pulled upward until it is firmly in place against the patient's chin. If a single set of ratchet teeth rows (188) and pawl (190) are present, no further operation is necessary. However, if a reverse ratchet teeth (202) and reverse pawl (204) is present, the tab (206) secured to the reverse pawl is pulled such that the reverse pawl (204) and the row of reverse ratchet teeth (202) interact, thus preventing further upward movement of the sternum and shoulder brace. Tabs (206) connected to both pawls are then locked in place against the cover piece (192). By this mechanism additional upward or downward movement of the sternum and shoulder brace is prevented. After the user no longer needs the cervical collar, the hook and loop material strip used as a collar retaining element is removed from the fasteners attached to the frontal portion and the frontal end portion. This removes the cervical collar from the patient's neck.

I claim:

1. An adjustable cervical collar comprising:
   (a) a chin support brace, and
   (b) an adjustment system means secured to said chin support brace and adjustably secured to an asymmetrical elongated neck encircling band opposite said chin support brace, said elongated neck encircling band containing as an integral element thereof a sternum and shoulder brace, whereby the height of the chin support brace can be adjusted relative to the elongated neck encircling band.

2. The collar of claim 1 further comprising a positive alignment means secured to the chin support brace for maintaining the chin support brace in parallel alignment with the elongated neck encircling band as the height of the chin support brace is adjusted in relation to the elongated neck encircling band.

3. The collar of claim 2 wherein the adjustment system means is a chin support height adjustment piece.

4. The collar of claim 3 wherein the chin support brace is a separate element from the chin support height adjustment piece.

5. The collar of claim 4 wherein the chin support brace is a preformed, bowed forward chin support brace.

6. The collar of claim 3 wherein the chin support brace is formed as one integral piece permanently secured to the chin support height adjustment piece.

7. The collar of claim 6 wherein the chin support brace is a preformed, bowed forward chin support brace.

8. The collar of claim 1 wherein the adjustment system means is a chin support height adjustment piece.

9. The collar of claim 8 wherein the chin support brace is a separate element from the chin support height adjustment piece.

10. The collar of claim 4 wherein the chin support brace is a preformed, bowed forward chin support brace.

11. The collar of claim 8 wherein the chin support brace is formed as one integral piece permanently secured to the chin support height adjustment piece.

12. The collar of claim 11 wherein the chin support brace is a preformed, bowed forward chin support brace.

13. The collar of claim 1 wherein the elongated neck encircling band is of one piece construction and further comprises a back portion, a back side portion, and a front end portion.

14. The collar of claim 13 wherein the elongated neck encircling band, including the integral sternum and shoulder brace, and the chin support brace, when secured together, are capable of being bent from a flat condition to a condition encircling the neck of a wearer.

15. The collar of claim 14 wherein the sternum and shoulder brace when placed flat is curvilinear in design, curving downward and then curving back upward from the front end portion to the back portion with an opposite longitudinal curved edge that runs from one side of the front end portion to the other side.

16. The collar of claim 14 wherein the parallel alignment is maintained between said secured together chin support brace and said elongated neck encircling band in both said flat condition and said condition encircling the neck of said wearer.

17. The collar of claim 13 wherein the back portion is secured to one side of the adjustment system means.

18. The collar of claim 13 wherein the back side portion is an integral part of the back portion and located distal from the sternum and shoulder brace.

19. The collar of claim 13 wherein the front end portion extends out from the sternum and shoulder brace and is distal from the back side portion.

20. The collar of claim 1 wherein the chin support brace is a two-piece chin support brace comprised of a first and a second chin support element wherein each chin support element has a first and second end where the first end of each said first and second chin support element is secured in place to the elongated neck encircling band and second ends of each said first and second chin support element are rotatably secured to the neck encircling band wherein the second and first chin support element overlaps the second end of the second chin support element to permit the two-piece chin support brace to be held in bowed forward position.

* * * * *